US012692268B2

(12) United States Patent
Hah et al.

(10) Patent No.: US 12,692,268 B2
(45) Date of Patent: Jul. 28, 2026

(54) IMIDAZOLE DERIVATIVE HAVING PROTEIN KINASE INHIBITORY ACTIVITY, AND USE THEREOF

(71) Applicant: INDUSTRY-UNIVERSITY COOPERATION FOUNDATION HANYANG UNIVERSITY ERICA CAMPUS, Ansan-si (KR)

(72) Inventors: Jung Mi Hah, Ansan-si (KR); Mi Young Jang, Ansan-si (KR)

(73) Assignee: INDUSTRY-UNIVERSITY COOPERATION FOUNDATION HANYANG UNIVERSITY ERICA CAMPUS (KR)

( * ) Notice: Subject to any disclaimer, the term of this patent is extended or adjusted under 35 U.S.C. 154(b) by 877 days.

(21) Appl. No.: 17/760,472

(22) PCT Filed: Feb. 24, 2021

(86) PCT No.: PCT/KR2021/002321
§ 371 (c)(1),
(2) Date: Aug. 10, 2022

(87) PCT Pub. No.: WO2021/172871
PCT Pub. Date: Sep. 2, 2021

(65) Prior Publication Data
US 2023/0140395 A1 May 4, 2023

(30) Foreign Application Priority Data
Feb. 28, 2020 (KR) ........................ 10-2020-0025335

(51) Int. Cl.
*C07D 487/04* (2006.01)
*A61K 31/506* (2006.01)
(Continued)

(52) U.S. Cl.
CPC ............ *C07D 487/04* (2013.01); *A61P 25/16* (2018.01); *A61P 25/28* (2018.01)

(58) Field of Classification Search
CPC ......... C07D 487/04; A61P 25/16; A61P 25/28
See application file for complete search history.

(56) References Cited

U.S. PATENT DOCUMENTS

| | | | | |
|---|---|---|---|---|
| 8,569,306 | B2 | 10/2013 | Buettelmann et al. | |
| 10,781,201 | B2 | 9/2020 | Hah et al. | |
| 2020/0039959 | A1* | 2/2020 | Hah .................... | C07D 403/14 |

FOREIGN PATENT DOCUMENTS

| | | | |
|---|---|---|---|
| KR | 101840674 | B1 | 3/2018 |
| KR | 20200011388 | A | 2/2020 |

(Continued)

OTHER PUBLICATIONS

Jang, M et al. Int. J. Mol. Sci. 2020, 21, 1698. (Year: 2020).*
(Continued)

*Primary Examiner* — Clinton A Brooks
*Assistant Examiner* — Kendall Nicole Heitmeier
(74) *Attorney, Agent, or Firm* — Myers Bigel, P.A.

(57) ABSTRACT

The present invention relates to: a novel imidazole derivative compound; an isomer thereof or a pharmaceutically acceptable salt thereof, and a pharmaceutical composition including the same. An imidazole derivative compound according to the present invention exhibits selective inhibitory activity against JNK, particularly JNK3, and thus can be used as a pharmaceutical composition for preventing and treating a degenerative brain disease (degenerative brain disease including Alzheimer's dementia, and Parkinson's disease).

13 Claims, 1 Drawing Sheet

(51) Int. Cl.

| | |
|---|---|
| ***A61P 25/16*** | (2006.01) |
| ***A61P 25/28*** | (2006.01) |
| ***C07D 471/04*** | (2006.01) |
| ***C07D 519/00*** | (2006.01) |

(56) References Cited

FOREIGN PATENT DOCUMENTS

| | | | |
|---|---|---|---|
| WO | 2010069833 | A1 | 6/2010 |
| WO | 2020022787 | A1 | 1/2020 |

OTHER PUBLICATIONS

American Chemical Society. Chemical Abstract Service. RN 2493287-83-3, Entered into STN Oct. 22, 2020 (Year: 2020).*

Musi, C. A. et al. Cells, 2020, 9(10) 2190. (Year: 2020).*

English translation of International Search Report corresponding to International Patent Application No. PCT/KR2021/002321 (2 pages) (mailed Jun. 4, 2021).

Jang et al. "Discovery of 1-Pyrimidinyl-2-Aryl-4,6-Dihydropyrrolo [3,4-d]Imidazole-5(1H)-Carboxamide as a Novel JNK Inhibitor" International Journal of Molecular Sciences, 21:1698, pp. 1-17 (2020).

* cited by examiner

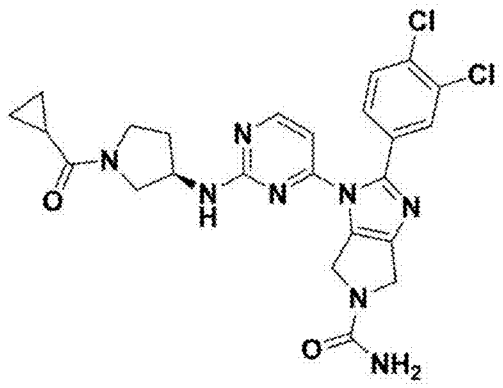
16c
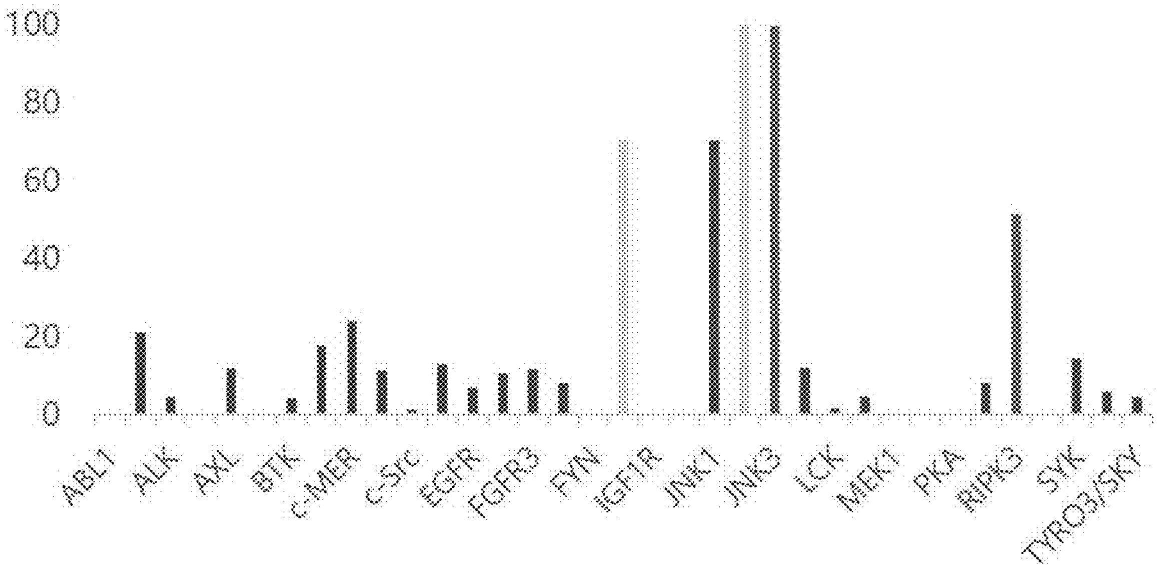

IMIDAZOLE DERIVATIVE HAVING PROTEIN KINASE INHIBITORY ACTIVITY, AND USE THEREOF

TECHNICAL FIELD

The present invention relates to a novel imidazole derivative having protein kinase c-Jun N-terminal Kinase 3 (JNK3) inhibitory activity, and a use thereof.

The present invention was made under the support of the Ministry of Science and ICT (2017Y) of the Republic of Korea with the project number 201900000002259, the research management institution for the project is the "National Research Foundation of Korea", the research business title is "Core Technology Development Project/Bio & Medical Technology Development Project/Research Program for New Drug Target Identification and Validation", the research project title is "Validation of INK inhibitor having effects of suppressing nerve cell apoptosis and improving cognitive function as therapeutic agent for Alzheimer's disease", and the research period is "Jun. 1, 2019 to Feb. 29, 2020".

The present patent application claims priority to and the benefit of Korean Patent Application No. 10-2020-0025335, filed on Feb. 28, 2020, the disclosure of which is incorporated herein by reference in its entirety.

BACKGROUND ART

Among the MAPK pathways which are representative cell signaling systems that regulate the apoptosis of cells, c-Jun N-terminal kinase (INK) is located at the end of the signaling system, and thus has been validated as a target in association with many diseases. Although JNK1 has been studied focusing on the link with metabolic diseases, the distribution of JNK3 isoforms is concentrated in brain tissues, unlike 10 isozymes of the same type, so that its association with nerve cell apoptosis has been studied. The distribution of JNK3 is conspicuous in the pyramidal neurons (yellow) located in the CA1 and CA2 regions of the hippocampus of the cerebral cortex of the human central nervous system (CNS), and here, JNK3 plays an overall role in the apoptosis of nerve cells. It is known that overexpression of c-Jun, which is one of the substrates of JNK3, the degree of phosphorylation by JNK3, hyperactivation of JNK3, and the like cause trophic factor withdrawal and apoptosis in nerve cells. Among degenerative brain diseases, the representative symptoms of Alzheimer's disease are the deposition of beta amyloid (Ab 42) in nerve cells, the generation of neurofibrillary tangles (NFTs), and the resulting apoptosis of nerve cells and synapses, and JNK3 has been shown to act both before and after such pathological phenomena.

JNK3 phosphorylates and activates amyloid precursor protein (APP) that produces beta-amyloid peptides, which are the main cause of Alzheimer's disease, to locate the APP in the cell membrane and promote its conversion to Ab 42. In particular, the position of phosphorylated APP in the cell membrane during this process is known to play a decisive role in the production of Ab 42, and Tau, which is the main component of NFTs found in the brain cells of patients with Alzheimer's disease, is also phosphorylated by JNK. It has been reported that JNK3 is increased 40% or more in the brain tissue of patients with Alzheimer's disease compared to normal subjects, and when JNK3 is inhibited or removed in a mouse model of Alzheimer's disease, the production of (JNK3 KO mouse) beta-amyloid is reduced 90% or more and cognitive function is improved to 80% of the normal level.

Further, it was observed that when jnk3 was removed from mice with familial Alzheimer's disease (FAD), oligomeric Ab 42 was remarkably reduced and cognitive ability was increased. This conclusively shows that activation of JNK3 plays a major role even in the onset of Alzheimer's disease, which has a family history, and that JNK3 is the most important factor that gives positive feedback to the production of Ab 42.

Mice from which a JNK3 gene had been removed showed clear resistance to MPTP, a toxic substance that causes Parkinson's disease, when administered, and do not show side effects (attacks or nerve cell apoptosis) caused by the introduction of neurotoxic substances (glutamate analogs) into the hippocampus of the cerebral cortex. JNK3 isomers are also known to be involved in ischaemic injury due to hyperactivation of glutamate receptors.

Degenerative brain disease is a representative geriatric disease, and although many studies have been conducted on its therapeutic goals, there are not many cases that describe a protein kinase, which is mainly known as an anticancer agent target. Although a protein kinase called GSK has been discussed in association with Alzheimer's disease, the protein kinase is in a state of retrogression because an inhibitor thereof cannot secure a direct effect.

Due to these selectivity issues and insufficient effects, interest in research to find JNK3 selective inhibitors has increased.

DISCLOSURE

Technical Problem

The present invention has been made to solve the problem as described above, and as a result of intensive studies to find a novel substance which is likely to be developed as a therapeutic agent for a degenerative brain disease such as Alzheimer's dementia, Parkinson's disease and Huntington's disease, the present inventors confirmed a novel imidazole derivative showing JNK3 inhibitory activity, thereby completing the present invention based on this.

Thus, an object of the present invention is to provide a novel imidazole derivative having JNK3 inhibitory activity, or a pharmaceutically acceptable salt thereof.

Another object of the present invention is to provide a method for preparing a novel imidazole derivative having JNK3 inhibitory activity.

Still another object of the present invention is to provide a pharmaceutical composition for preventing or treating a degenerative brain disease, including the imidazole derivative or a pharmaceutically acceptable salt thereof as an active ingredient.

Yet another object of the present invention is to provide a method for treating a degenerative brain disease, the method including: administering the imidazole derivative or a pharmaceutically acceptable salt thereof to an individual or subject in need thereof.

Yet another object of the present invention is to provide the imidazole derivative or a pharmaceutically acceptable salt thereof for use in the treatment of a degenerative brain disease.

Yet another object of the present invention is to provide a use of the imidazole derivative or a pharmaceutically acceptable salt thereof for use in the preparation of a medicament for a degenerative brain disease.

However, technical problems to be solved by the present invention are not limited to the aforementioned problems, and other problems that are not mentioned may be clearly understood by those skilled in the art from the following description.

Technical Solution

To achieve the aforementioned objects of the present invention, provided is a compound represented by the following Chemical Formula 1 or a pharmaceutically acceptable salt thereof.

[Chemical Formula 1]

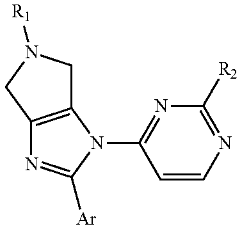

In Chemical Formula 1, $R_1$ is selected from the group consisting of

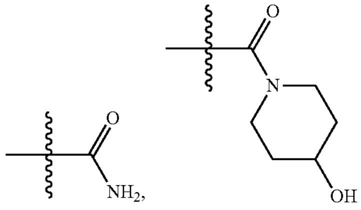

and a $C_1$-$C_6$ alkyl, $R_2$ is

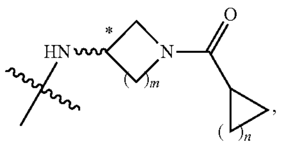

herein, n is an integer from 1 to 4, m is an integer from 2 to 3, carbon denoted as * is a chiral carbon, Ar is selected from the group consisting of

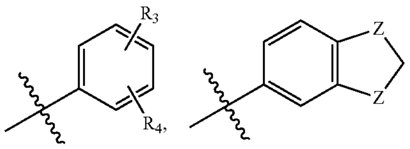

and naphthalenyl, $R_3$ and $R_4$ are each independently a halogen atom, and Z is a carbon or oxygen atom.

Further, the present invention provides a pharmaceutical composition for preventing or treating a degenerative brain disease, including the derivative of Chemical Formula 1 or a pharmaceutically acceptable salt thereof as an active ingredient.

As an exemplary embodiment of the present invention, the composition may inhibit the activity of c-Jun N-terminal kinase 3 (JNK3).

Advantageous Effects

Since a novel imidazole derivative or a pharmaceutically acceptable salt thereof according to the present invention exhibits excellent inhibitory activity against c-Jun N-terminal kinase 3 (JNK 3) as a target, a pharmaceutical composition including the derivative can be usefully used for the prevention and treatment of a degenerative brain disease including Alzheimer's dementia.

DESCRIPTION OF DRAWINGS

FIG. 1 is a graph showing the results of screening the kinase panel of Compound 16c.

MODES OF THE INVENTION

Hereinafter, the present invention will be described in detail.

The present invention provides a compound of the following Chemical Formula 1, or a pharmaceutically acceptable salt thereof.

[Chemical Formula 1]

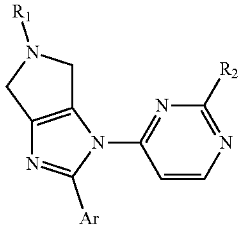

In Chemical Formula 1, $R_1$ is selected from the group consisting of

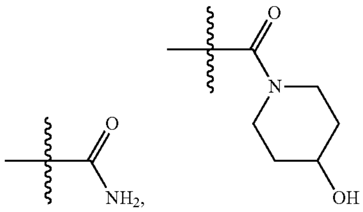

and a $C_1$-$C_6$ alkyl, $R_2$ is

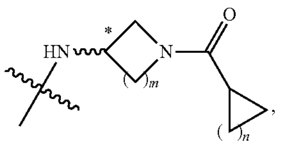

herein, n is an integer from 1 to 4, m is an integer from 2 to 3, carbon denoted as * is a chiral carbon, Ar is selected from the group consisting of

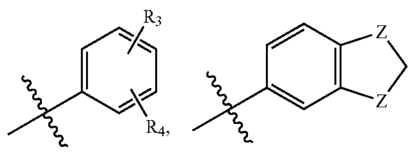

and naphthalenyl, $R_3$ and $R_4$ are each independently a halogen atom, and

Z is a carbon or oxygen atom.

As used herein, the term "chiral" is referred to as chirality or handedness, and is also referred to as an enantiomer or an optical isomer. Enantiomers are mirror images of each other.

As used herein, the term "alkyl" refers to a straight or branched saturated hydrocarbon group generally having a specified number of carbon atoms (for example, 1 to 12 carbon atoms). Examples of an alkyl group include methyl, ethyl, n-propyl, isopropyl, n-butyl, sec-butyl, isobutyl, tert-butyl, n-pentyl, n-hexyl, n-heptyl, and the like without limitation. An alkyl may be attached to a parent group or a substrate at any ring atom provided that the attachment does not violate valence requirements. Similarly, an alkyl group or an alkenyl group may include one or more non-hydrogen substituents provided that the attachment does not violate valence requirements.

As used herein, the term "Halogen" is an element belonging to Group 17 of the Periodic Table, and includes fluorine, chlorine, bromine, iodine, and the like.

In an exemplary embodiment of the present invention, the compound of Chemical Formula 1 may be a compound having a structure of the following Chemical Formula 2.

[Chemical Formula 2]

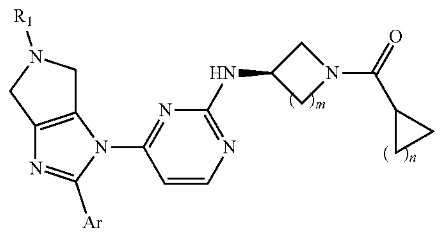

In Chemical Formula 2, $R_1$ is selected from the group consisting of

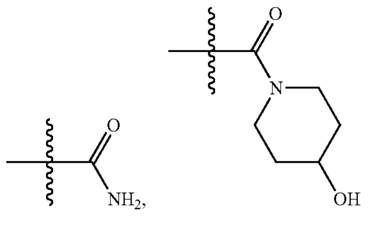

and a $C_1$-$C_6$ alkyl, n is an integer from 1 to 4, m is an integer from 2 to 3, Ar is selected from the group consisting of

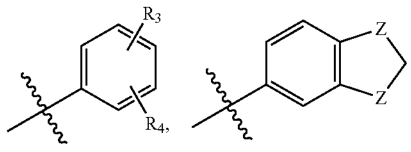

and naphthalenyl, $R_3$ and $R_4$ are each independently a halogen atom, and

Z is a carbon or oxygen atom.

As another exemplary embodiment of the present invention, the compound of Chemical Formula 1 may be a compound having a structure of the following Chemical Formula 3.

[Chemical Formula 3]

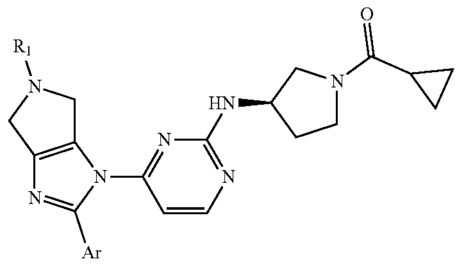

In Chemical Formula 3, $R_1$ is selected from the group consisting of

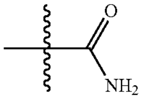

and a $C_1$-$C_6$ alkyl,

Ar is selected from the group consisting of

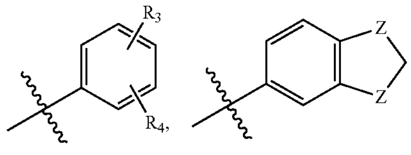

and naphthalenyl, $R_3$ and $R_4$ are each independently a halogen atom, and

Z is a carbon or oxygen atom.

As still another exemplary embodiment of the present invention, the compound of Chemical Formula 1 may be a compound having a structure of the following Chemical Formula 4.

[Chemical Formula 4]

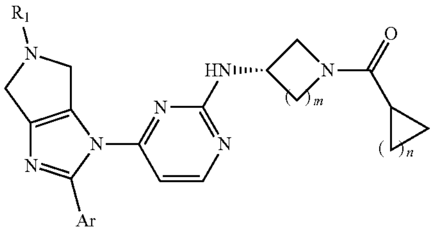

In Chemical Formula 4, $R_1$ is selected from the group consisting of

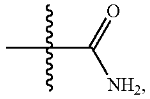

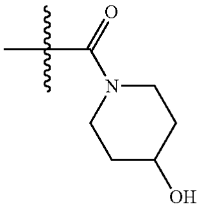

and a $C_1$-$C_6$ alkyl, n is an integer from 1 to 4, m is an integer from 2 to 3, Ar is selected from the group consisting of

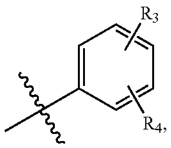

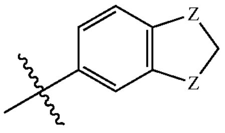

and naphthalenyl, $R_3$ and $R_4$ are each independently a halogen atom, and

Z is a carbon or oxygen atom.

As yet another exemplary embodiment of the present invention, the compound of Chemical Formula 1 may be a compound having a structure of the following Chemical Formula 5.

[Chemical Formula 5]

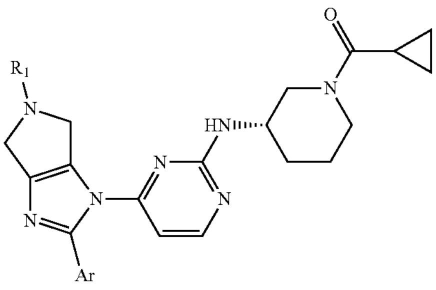

In Chemical Formula 5, $R_1$ is selected from the group consisting of

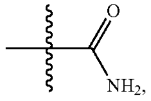

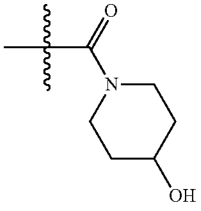

and a $C_1$-$C_6$ alkyl,

Ar is selected from the group consisting of

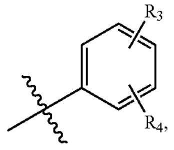

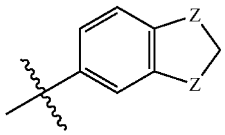

and naphthalenyl, $R_3$ and $R_4$ are each independently a halogen atom, and

Z is a carbon or oxygen atom.

As yet another exemplary embodiment of the present invention, the compound of Chemical Formula 1 may be a compound having a structure of the following Chemical Formula 6.

[Chemical Formula 6]

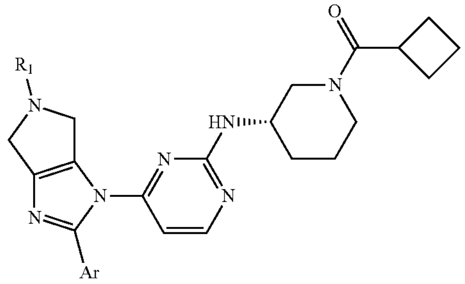

In Chemical Formula 6, $R_1$ is selected from the group consisting of

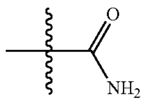 [SMILES: *C(N)=O]

and a $C_1$-$C_6$ alkyl,

Ar is selected from the group consisting of

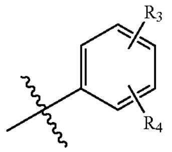

and

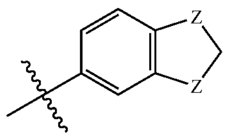

, $R_3$ and $R_4$ are each independently a halogen atom, and

Z is a carbon or oxygen atom.

As yet another exemplary embodiment of the present invention, the compound of Chemical Formula 1 may be a compound having a structure of the following Chemical Formula 7.

[Chemical Formula 7]

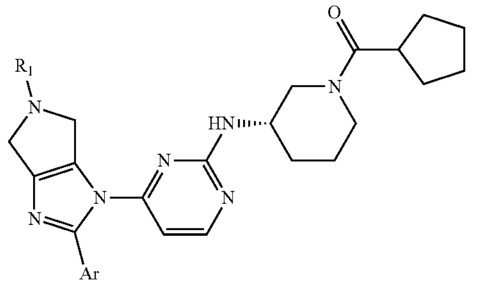

In Chemical Formula 7, $R_1$ is selected from the group consisting of

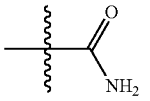 [SMILES: *C(N)=O]

and a $C_1$-$C_6$ alkyl,

Ar is

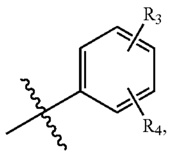

$R_3$ and $R_4$ are each independently a halogen atom, and

Z is a carbon or oxygen atom.

As yet another exemplary embodiment of the present invention, the compound of Chemical Formula 1 may be a compound having a structure of the following Chemical Formula 8.

[Chemical Formula 8]

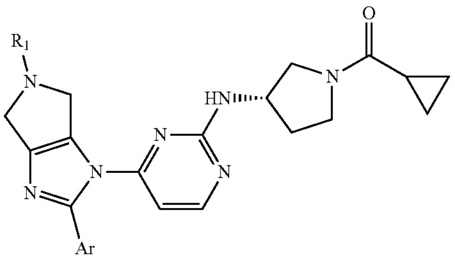

In Chemical Formula 8, $R_1$ is selected from the group consisting of

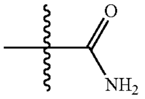 [SMILES: *C(N)=O]

and a $C_1$-$C_6$ alkyl,

Ar is selected from the group consisting of

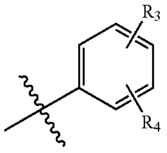 and 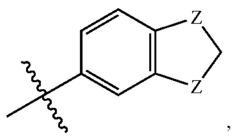 , $R_3$ and $R_4$ are each independently a halogen atom, and Z is a carbon or oxygen atom.

As yet another exemplary embodiment of the present invention, the imidazole compound of Chemical Formula 1 may be:

(S)-(1-(2-((1-(cyclopropanecarbonyl)piperidin-3-yl)amino)pyrimidin-4-yl)-2-(3,4-dichlorophenyl)-4,6-dihydropyrrolo[3,4-d]imidazol-5(1H)-yl)(4-hydroxypiperidin-1-yl)methanone;

(S)-(1-(2-((1-(cyclopropanecarbonyl)piperidin-3-yl)amino)pyrimidin-4-yl)-2-(3,4-dichlorophenyl)-4,6-dihydropyrrolo[3,4-d]imidazole-5(1H)-carboxamide;

(R)-1-(2-((1-(cyclopropanecarbonyl)pyrrolidin-3-yl)amino)pyrimidin-4-yl)-2-(3,4-dichlorophenyl)-4,6-dihydropyrrolo[3,4-d]imidazole-5(1H)-carboxamide;

(S)-1-(2-((1-(cyclopropanecarbonyl)pyrrolidin-3-yl)amino)pyrimidin-4-yl)-2-(3,4-dichlorophenyl)-4,6-dihydropyrrolo[3,4-d]imidazole-5(1H)-carboxamide;

(S)-1-(2-((1-(cyclobutanecarbonyl)piperidin-3-yl)amino)pyrimidin-4-yl)-2-(3,4-dichlorophenyl)-4,6-dihydropyrrolo[3,4-d]imidazole-5(1H)-carboxamide;

(S)-1-(2-((1-(cyclopentanecarbonyl)piperidin-3-yl)amino)pyrimidin-4-yl)-2-(3,4-dichlorophenyl)-4,6-dihydropyrrolo[3,4-d]imidazole-5(1H)-carboxamide;

(S)-1-(2-((1-(cyclopropanecarbonyl)piperidin-3-yl)amino)pyrimidin-4-yl)-2-(naphthalen-2-yl)-4,6-dihydropyrrolo[3,4-d]imidazole-5(1H)-carboxamide;

(R)-1-(2-((1-(cyclopropanecarbonyl)pyrrolidin-3-yl)amino)pyrimidin-4-yl)-2-(naphthalen-2-yl)-4,6-dihydropyrrolo[3,4-d]imidazole-5(1H)-carboxamide;

(S)-1-(2-((1-(cyclopropanecarbonyl)pyrrolidin-3-yl)amino)pyrimidin-4-yl)-2-(3,4-dichlorophenyl)-4,6-dihydropyrrolo[3,4-d]imidazole-5(1H)-carboxamide;

(S)-2-(benzo[d][1,3]dioxol-5-yl)-1-(2-((1-(cyclopropanecarbonyl)piperidin-3-yl)amino)pyrimidin-4-yl)-4,6-dihydropyrrolo[3,4-d]imidazole-5(1H)-carboxamide;

(R)-2-(benzo[d][1,3]dioxol-5-yl)-1-(2-((1-(cyclopropanecarbonyl)pyrrolidin-3-yl)amino)pyrimidin-4-yl)-4,6-dihydropyrrolo[3,4-d]imidazole-5(1H)-carboxamide;

(S)-2-(benzo[d][1,3]dioxol-5-yl)-1-(2-((1-(cyclopropanecarbonyl)pyrrolidin-3-yl)amino)pyrimidin-4-yl)-4,6-dihydropyrrolo[3,4-d]imidazole-5(1H)-carboxamide;

(S)-2-(benzo[d][1,3]dioxol-5-yl)-1-(2-((1-(cyclobutanecarbonyl)piperidin-3-yl)amino)pyrimidin-4-yl)-4,6-dihydropyrrolo[3,4-d]imidazole-5(1H)-carboxamide;

(S)-1-(2-((1-(cyclopropanecarbonyl)piperidin-3-yl)amino) pyrimidin-4-yl)-2-(2,3-dihydrobenzofuran-5-yl)-4,6-dihydropyrrolo[3,4-d]imidazole-5(1H)-carboxamide;

(R)-1-(2-((1-(cyclopropanecarbonyl)pyrrolidin-3-yl)amino) pyrimidin-4-yl)-2-(2,3-dihydrobenzofuran-5-yl)-4,6-dihydropyrrolo[3,4-d]imidazole-5(1H)-carboxamide; or (S)-1-(2-((1-(cyclopropanecarbonyl)pyrrolidin-3-yl)amino) pyrimidin-4-yl)-2-(2,3-dihydrobenzofuran-5-yl)-4,6-dihydropyrrolo[3,4-d]imidazole-5(1H)-carboxamide.

The present invention provides a pharmaceutical composition for preventing or treating a degenerative brain disease, including the derivative of Chemical Formula 1 or a pharmaceutically acceptable salt thereof as an active ingredient.

As another exemplary embodiment of the present invention, the degenerative brain disease may be Alzheimer's dementia or Parkinson's disease.

As still another exemplary embodiment of the present invention, the composition may inhibit the activity of c-Jun N-terminal kinase 3 (JNK3).

Meanwhile, the compound of the present invention may be used in the form of a pharmaceutically acceptable salt, and as the salt, an acid addition salt formed by a pharmaceutically acceptable free acid is useful.

As used herein, the term "salt" may be an acid addition salt formed by a pharmaceutically acceptable free acid. The acid addition salt is obtained from inorganic acids such as hydrochloric acid, nitric acid, phosphoric acid, sulfuric acid, hydrobromic acid, hydroiodic acid, nitrous acid or phosphorous acid, and nontoxic organic acids such as aliphatic mono- and dicarboxylates, phenyl-substituted alkanoates, hydroxyalkanoates and alkanedioates, aromatic acids, aliphatic and aromatic sulfonic acids. Such pharmaceutically nontoxic salts include sulfates, pyrosulfates, bisulfates, sulfites, bisulfites, nitrates, phosphates, monohydrogen phosphates, dihydrogen phosphates, metaphosphates, pyrophosphates, chlorides, bromides, iodides, fluorides, acetates, propionates, decanoates, caprylates, acrylates, formates, isobutyrates, caprates, heptanoates, propiolates, oxalates, malonates, succinates, suberates, sebacates, fumarates, maleates, butene-1,4-dioates, hexane-1,6-dioates, benzoates, chlorobenzoates, methyl benzoates, dinitrobenzoates, hydroxybenzoates, methoxybenzoates, phthalates, terephthalates, benzenesulfonates, toluenesulfonates, chlorobenzenesulfonates, xylenesulfonates, phenyl acetates, phenyl propionates, phenyl butyrates, citrates, lactates, β-hydroxybutyrates, glycolates, malates, tartrates, methanesulfonates, propanesulfonates, naphthalene-1-sulfonates, naphthalene-2-sulfonates or mandelates.

The acid addition salt according to the present invention may be prepared by typical methods, for example, dissolving the compound in an excess aqueous acid solution, and precipitating the salt using a water-miscible organic solvent, for example, methanol, ethanol, acetone or acetonitrile. Further, the acid addition salt may also be prepared by evaporating the solvent or excess acid from this mixture, and then drying the mixture or suction-filtering a precipitated salt.

In addition, a pharmaceutically acceptable metal salt may be prepared using a base. An alkali metal or alkaline earth metal salt is obtained by, for example, dissolving the compound in an excess alkali metal hydroxide or alkaline-earth metal hydroxide solution, filtering the non-soluble compound salt, evaporating the filtrate, and drying the result product. In this case, preparing a sodium, potassium or calcium salt as the metal salt is pharmaceutically suitable. A silver salt corresponding to this is obtained by reacting the alkali metal or alkaline earth metal salt with a suitable silver salt (for example, silver nitrate).

Further, the compound of the present invention includes not only pharmaceutically acceptable salts, but also all salts, isomers, hydrates and solvates which can be prepared by typical methods.

As can be confirmed in the following Examples, the compound of Chemical Formula 1 may be used as a JNK3 inhibitor, and as described in the Background Art of the invention, it is well known to those skilled in the art that the JNK3 inhibitor can be used for the treatment of a degenerative brain disease.

The present invention provides a pharmaceutical composition for preventing or treating a degenerative brain disease, including the imidazole derivative of Chemical Formula 1 or a pharmaceutically acceptable salt thereof as an active ingredient, and more specifically, a pharmaceutical composition for preventing or treating a degenerative brain disease, a use of the imidazole derivative of Chemical Formula 1 or a pharmaceutically acceptable salt thereof for treating the disease, and a method for treating the disease, the method including: administering a therapeutically effective amount of the compound of Chemical Formula 1 or a pharmaceutically acceptable salt thereof to a subject.

As used herein, the term "prevention" refers to all actions that suppress a degenerative brain disease or delay the onset of the degenerative brain disease by administering the pharmaceutical composition according to the present invention.

As used herein, the term "treatment" refers to all actions that ameliorate or beneficially change symptoms caused by a degenerative brain disease by administering the pharmaceutical composition according to the present invention.

The pharmaceutical composition of the present invention may include a pharmaceutically acceptable carrier in addition to an active ingredient. In this case, the pharmaceutically acceptable carrier is typically used during formulation, and includes lactose, dextrose, sucrose, sorbitol, mannitol, starch, gum acacia, calcium phosphate, alginate, gelatin, calcium silicate, microcrystalline cellulose, polyvinylpyrrolidinone, cellulose, water, syrup, methylcellulose, methyl hydroxybenzoate, propyl hydroxybenzoate, talc, magnesium stearate, mineral oil, and the like, but is not limited thereto. Furthermore, the pharmaceutically acceptable carrier may further comprise a lubricant, a wetting agent, a sweetening agent, a flavoring agent, an emulsifier a suspending agent, a preservative, and the like in addition to the above ingredients.

The pharmaceutical composition of the present invention may be orally administered or may be parenterally administered (for example, intravenously, subcutaneously, intraperitoneally, or topically applied), and the dosage may vary depending on a patient's condition and body weight, severity of disease, drug form, and administration route and period according to the desired method, but the dosage may be properly selected by the person skilled in the art.

The pharmaceutical composition of the present invention is administered in a pharmaceutically effective amount. As used herein, the "pharmaceutically effective amount" refers to an amount sufficient to treat diseases at a reasonable benefit/risk ratio applicable to medical treatment, and an effective dosage level may be determined according to factors including the type of a patient's disease, the severity of disease, the activity of drugs, sensitivity to drugs, administration time, administration route, excretion rate, treatment period, and simultaneously used drugs, and other factors well known in the medical field. The pharmaceutical composition according to the present invention may be administered as an individual therapeutic agent or in combination with other therapeutic agents, may be administered sequentially or simultaneously with therapeutic agents in the related art, and may be administered in a single dose or multiple doses. It is important to administer the composition in a minimum amount that can obtain the maximum effect without any side effects, in consideration of all the aforementioned factors, and this amount may be easily determined by those skilled in the art.

Specifically, an effective amount of the pharmaceutical composition of the present invention may vary depending on the age, gender, condition, and body weight of a patient, the absorption of the active ingredient in the body, inactivation rate and excretion rate, disease type, and the drugs used in combination, and in general, 0.0001 to 1000 mg, preferably 0.001 to 500 mg of the pharmaceutical composition of the present invention per 1 kg of body weight may be administered daily or every other day or may be dividedly administered once to three times a day. However, since the effective amount may be increased or decreased depending on the administration route, the severity of obesity, gender, body weight, age, and the like, the dosage is not intended to limit the scope of the present invention in any way.

In the present invention, "an individual" refers to a subject in need of treatment of a disease, and more specifically, refers to a mammal such as a human or a non-human primate, a mouse, a dog, a cat, a horse, and a cow.

Hereinafter, preferred preparation examples and examples for helping with understanding of the present invention will be suggested. However, the following examples are provided only to more easily understand the present invention, and the contents of the present invention are not limited by the following preparation examples.

<Preparation Example 1> Synthesis of tert-butyl 2,5-dihydro-1H-pyrrole-1-carboxylate (Compound 3)

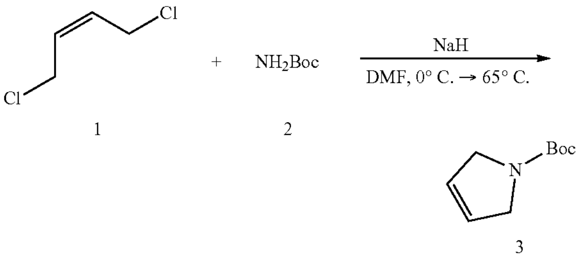

After Compound 2 (4.65 mmol) was dissolved in dimethylformamide (DMF, 5 ml), NaH (10.23 mmol) was added thereto at 0° C., and the resulting mixture was stirred for 10 minutes. Compound 1 was added to the mixture, and the resulting mixture was stirred at room temperature for 15 minutes, and then stirred at 65° C. for 4 to 6 hours. When there was no change in TLC over time, the mixture was cooled to ambient temperature, and an organic layer was extracted (EA:HEX=1:4) and washed with water. The organic layer was dried over anhydrous magnesium sulfate ($MgSO_4$) and the solvent was evaporated to obtain Compound 3 (45%).

$^1$H NMR (400 MHz, $CDCl_3$) δ 5.76 (s, 2H), 4.11 (s, 4H), 1.47 (s, 9H).

<Preparation Example 2> Tert-butyl (3R,4S)-3,4-dihydroxypyrrolidine-1-carboxylate (Compound 4)

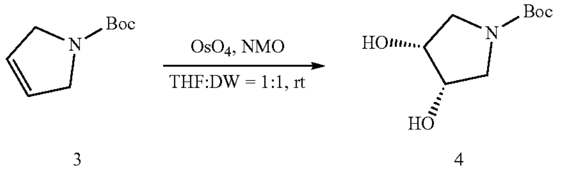

After Compound 3 (6.3 mmol) was dissolved in tetrahydrofuran (THF, 15.8 ml), a mixture in $OsO_4$ (0.113 mmol) and N-methylmorpholine-N-oxide (8.29 mmol) were dissolved in 15.8 ml of water was slowly added dropwise thereto, and then the resulting mixture was stirred at room temperature for 3 to 5 hours. When Compound 3 disappeared in TLC, the resulting product was concentrated under vacuum, then extracted with ethyl acetate (EtOAc) and washed with water. After the product was dried over anhydrous magnesium sulfate ($MgSO_4$) and the solvent was evaporated, the product was purified by column chromatography on silica gel using the mobile phase of EA:HEX (3:1) to obtain Compound 4 (59%).

$^1$H NMR (400 MHz, $CDCl_3$) δ 4.25 (qd, J=4.4, 2.1 Hz, 2H), 3.59 (dd, J=11.4, 5.7 Hz, 2H), 3.34 (dd, J=11.3, 3.8 Hz, 2H), 1.45 (s, 9H).

<Preparation Example 3> Tert-butyl (3R,4S)-3,4-bis((methylsulfonyl)oxy)pyrrolidine-1-carboxylate (Compound 5)

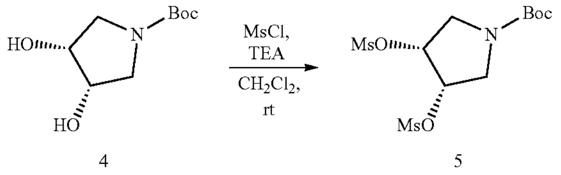 [SMILES: CC(C)(C)OC(=O)N1C[C@@H](O)[C@@H](O)C1 ; "MsCl,TEA" ; CC(C)(C)OC(=O)N1C[C@H](OS(C)(=O)=O)[C@H](OS(C)(=O)=O)C1]

After Compound 4 (0.96 mmol) was dissolved in dichloromethane (DCM, 4.8 ml), Methanesulfonyl chloride (MsCl, 2.11 mmol) and triethylamine (TEA, 2.11 mmol) were added thereto, and the resulting mixture was stirred at room temperature for 30 minutes to 1 hour. Compound 4 disappeared in TLC and the reaction mixture was washed with water and brine. The resulting product was dried over anhydrous magnesium sulfate ($MgSO_4$) and the solvent was evaporated to obtain Compound 5 (90%).

$^1$H NMR (400 MHz, $CDCl_3$) δ 5.17 (t, J=4.0 Hz, 2H), 3.84-3.74 (m, 2H), 3.68-3.59 (m, 2H), 3.14 (d, J=5.6 Hz, 6H), 1.46 (s, 9H).

<Preparation Example 4> Tert-butyl (3S,4R)-3,4-diazidopyrrolidine-1-carboxylate (Compound 6)

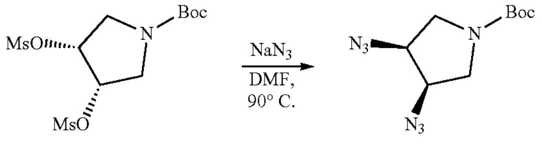

5
6

After Compound 5 (3.3 mmol) was dissolved in dimethylformamide (DMF, 33 ml), $NaN_3$ (33 mmol) was added thereto, and the resulting mixture was stirred at 90° C. for 24 hours. When Compound 5 disappeared in TLC, the mixture was cooled to ambient temperature, then extracted with ethyl acetate (EtOAc) and washed with brine. After the product was dried over anhydrous magnesium sulfate ($MgSO_4$) and the solvent was concentrated under vacuum, the product was purified by column chromatography on silica gel using the mobile phase of EA:HEX (1:4) to obtain Compound 6 (79%).

$^1H$ NMR (400 MHz, $CDCl_3$) δ 4.08 (d, J=3.3 Hz, 2H), 3.63 (dd, J=8.8, 5.5 Hz, 2H), 3.44 (ddd, J=16.3, 10.8, 4.1 Hz, 2H), 1.46 (s, 9H).

<Preparation Example 5> Tert-butyl (3S,4R)-3,4-diamidopyrrolidine-1-carboxylate (Compound 7)

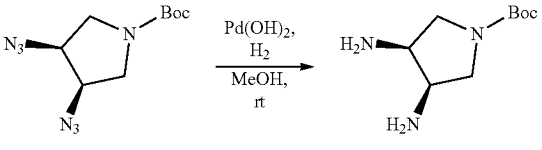

6
7

After Compound 6 (2.6 mmol) was dissolved in methanol (MeOH, 10.4 ml), palladium hydroxide on carbon (Pd(OH) $_2$, 0.52 mmol) was added thereto. The resulting mixture was stirred under hydrogen gas at room temperature for about 4 hours. When Compound 6 disappeared in TLC, the mixture was filtered with a Celite pad, and then the filtrate was concentrated to obtain Compound 7 (98%).

$^1H$ NMR (400 MHz, DMSO) δ 3.26 (dd, J=10.9, 5.9 Hz, 3H), 3.14 (dq, J=9.6, 4.8 Hz, 2H), 2.95 (dd, J=10.6, 4.9 Hz, 2H), 1.38 (s, 9H).

<Preparation Example 6> Tert-butyl (3aS,6aR)-2-(3,4-dichlorophenyl)-3a,4,6,6a-tetrahydropyrrolo-imidazole-5(1H)-carboxylate (Compound 9a-9f)

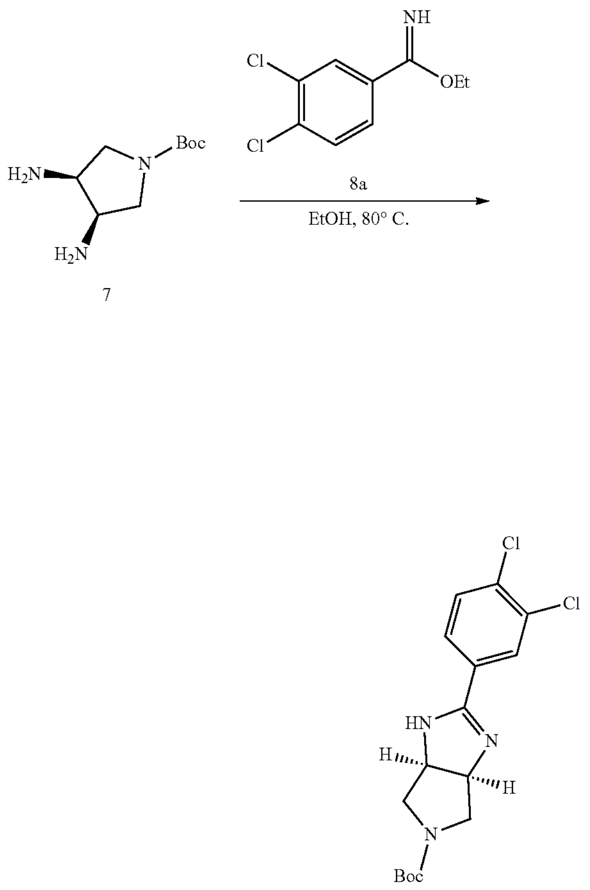

7
8a
9a-9f

After Compound 7 (2.69 mmol) and Compound 8a (2.5 mmol) were dissolved in ethanol (13.4 ml), the resulting solution was stirred at 80° C. for 1 hour to 2 hours. When Compound 8a disappeared in TLC, the mixture was cooled to ambient temperature, and then concentrated under vacuum. The concentrated mixture was extracted with ethyl acetate (EtOAc) and washed with brine. After the product was dried over anhydrous magnesium sulfate ($MgSO_4$) and the solvent was evaporated, the product was purified by column chromatography on silica gel using the mobile phase of EA:HEX (3:1) to obtain Compound 9a-9f (47%).

$^1H$ NMR (400 MHz, $CDCl_3$) δ 7.93 (d, J=2.0 Hz, 1H), 7.66 (dd, J=8.4, 2.0 Hz, 1H), 7.48 (d, J=8.4 Hz, 1H), 4.67 (s, 2H), 3.74 (d, J=12.2 Hz, 2H), 3.54 (dd, J=12.3, 6.5 Hz, 2H), 1.43 (s, 9H). $^1H$ NMR (400 MHz, MeOD) δ 7.96 (d, J=2.0 Hz, 1H), 7.71 (dd, J=8.4, 2.0 Hz, 1H), 7.63 (d, J=8.4 Hz, 1H), 4.65 (s, 2H), 3.71 (d, J=12.0 Hz, 2H), 3.55-3.44 (m, 2H), 1.43 (s, 9H).

<Preparation Example 7> Tert-butyl (3aS,6aR)-2-(naphthalen-2-yl)-3a,4,6,6a-tetrahydropyrrolo[3,4-d]imidazole-5(1H)-carboxylate (Compound 9g-9i)

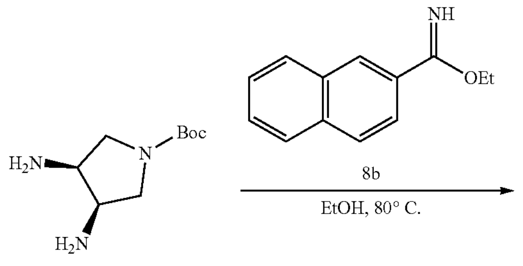

7

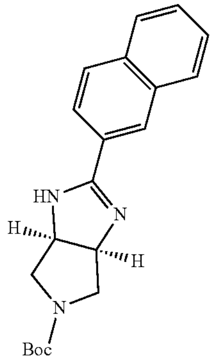

9g-9i

Compound 9a-9i (95%) was obtained by performing synthesis in the same manner as in Preparation Example 6.

$^1$H NMR (400 MHz, DMSO) δ 8.77 (d, J=1.4 Hz, 1H), 8.18 (d, J=8.7 Hz, 1H), 8.10-8.03 (m, 3H), 7.74 (ddd, J=14.4, 7.9, 1.2 Hz, 2H), 4.94 (d, J=1.4 Hz, 2H), 3.82 (d, J=12.5 Hz, 2H), 3.45 (d, J=12.4 Hz, 2H), 3.32 (s, 1H), 1.32 (s, 9H).

<Preparation Example 8> Tert-butyl (3aS,6aR)-2-(benzo[d][1,3]dioxol-5-yl)-3a,4,6,6a-tetrahydropyrrolo[3,4-d]imidazole-5(1H)-carboxylate (Compound 9j-9m)

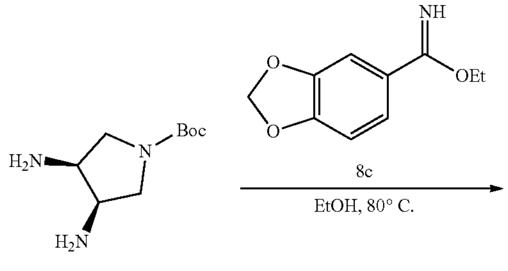

7

-continued

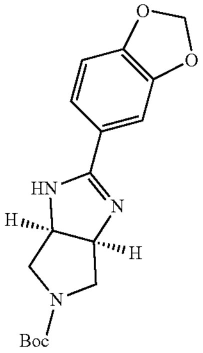

9j-9m

Compound 9j-9m (98%) was obtained by performing synthesis in the same manner as in Preparation Example 6.

$^1$H NMR (400 MHz, DMSO) δ 7.68 (d, J=11.4 Hz, 2H), 7.21 (d, J=8.1 Hz, 1H), 6.21 (s, 2H), 4.85 (s, 2H), 3.76 (d, J=12.5 Hz, 2H), 3.39 (d, J=12.1 Hz, 2H), 3.32 (s, 1H), 1.34 (s, 9H).

<Preparation Example 9> Tert-butyl (3aS,6aR)-2-(2,3-dihydrobenzofuran-5-yl)-3a,4,6,6a-tetrahydropyrrolo[3,4-d]imidazole-5(1H)-carboxylate (Compound 9n-9p)

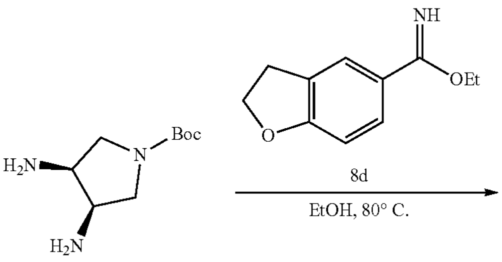

7

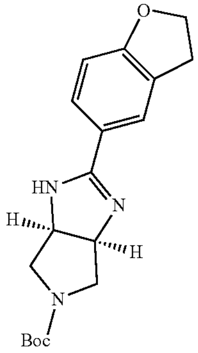

9n-9p

Compound 9n-9p (98%) was obtained by performing synthesis in the same manner as in Preparation Example 6.

$^1$H NMR (400 MHz, $CDCl_3$) δ 8.15 (s, 1H), 8.08 (d, J=8.5 Hz, 1H), 6.74 (d, J=8.5 Hz, 1H), 4.85 (s, 2H), 4.62 (t, J=8.8 Hz, 2H), 4.01 (d, J=12.5 Hz, 2H), 3.44 (d, J=12.1 Hz, 2H), 3.18 (t, J=8.7 Hz, 2H), 1.39 (s, 9H).

<Preparation Example 10> Tert-butyl-2-(3,4-dichlorophenyl)-4,6-dihydropyrrolo[3,4-d]imidazole-5(1H)-carboxylate (Compound 10a-10f)

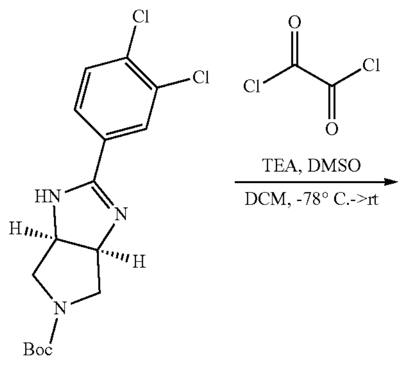

9

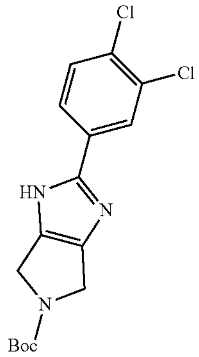

10a-10f

After oxalyl chloride (0.59 mmol) and dimethyl sulfoxide (DMSO, 1.18 mmol) were dissolved in 7 ml of dichloromethane and the resulting solution was stirred at −78° C. for 10 minutes, Compound 9 (0.59 mmol) dissolved in 5 ml of dichloromethane at −78° C. was added thereto, and the resulting mixture was stirred for 30 minutes. Thereafter, triethylamine (5.9 mmol) was slowly added thereto, and then the resulting mixture was stirred at RT for 1 hour and 30 minutes. When Compound 9 disappeared in TLC, the reaction mixture was washed with water and brine. The resulting product was dried over anhydrous magnesium sulfate ($MgSO_4$) and the solvent was concentrated under vacuum to obtain Compound 10a-10f (50%).

$^1$H NMR (400 MHz, DMSO) δ 12.82 (d, J=24.4 Hz, 1H), 8.41 (s, 1H), 8.07 (d, J=8.6 Hz, 1H), 7.99-7.88 (m, 3H), 7.59-7.48 (m, 2H), 4.50 (s, 2H), 4.33 (d, J=10.1 Hz, 2H), 1.47 (s, 9H).

<Preparation Example 11> Tert-butyl-2-(naphthalen-2-yl)-4,6-dihydropyrrolo[3,4-d]imidazole-5(1H)-carboxylate (Compound 10g-10i)

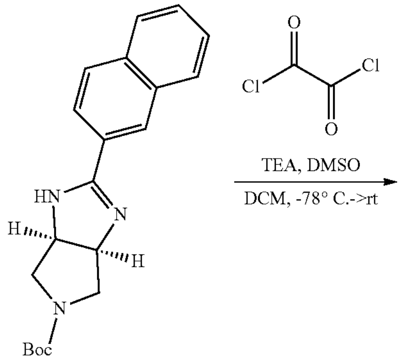

9

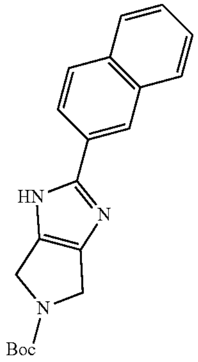

10g-10i

Compound 10g-10f (51%) was obtained by performing synthesis and purification in the same manner as in Preparation Example 10.

$^1$H NMR (400 MHz, DMSO) δ 12.82 (d, J=24.4 Hz, 1H), 8.41 (s, 1H), 8.07 (d, J=8.6 Hz, 1H), 7.99-7.88 (m, 3H), 7.59-7.48 (m, 2H), 4.50 (s, 2H), 4.33 (d, J=10.1 Hz, 2H), 1.47 (s, 9H).

<Preparation Example 12> Tert-butyl-2-(benzo[d][1,3]dioxol-5-yl)-4,6-dihydropyrrolo[3,4-d]imidazole-5(1H)-carboxylate (Compound 10j-10m)

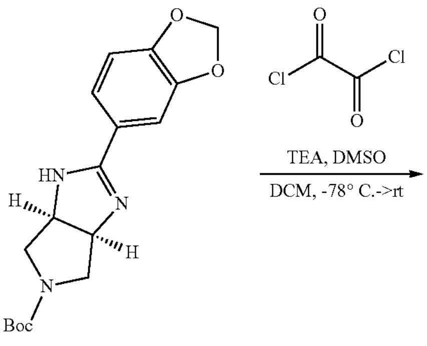

9

-continued

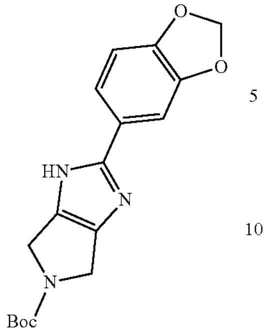

10j-10m

Compound 10j-10m (50%) was obtained by performing synthesis and purification in the same manner as in Preparation Example 10.

$^1$H NMR (400 MHz, $CDCl_3$) δ 7.32 (dd, J=10.6, 1.6 Hz, 2H), 6.81 (d, J=8.0 Hz, 1H), 5.99 (s, 2H), 4.49-4.39 (m, 4H), 1.51 (s, 9H).

<Preparation Example 13> Tert-butyl-2-(2,3-dihydrobenzofuran-5-yl)-4,6-dihydropyrrolo[3,4-d]imidazole-5(1H)-carboxylate (Compound 10n-10p)

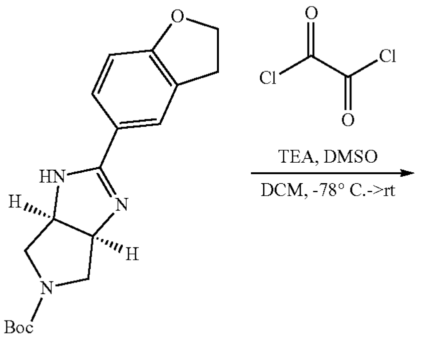

9

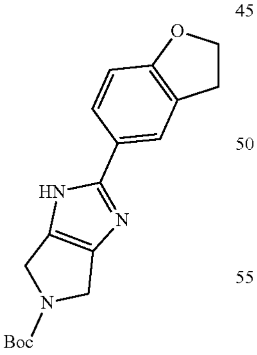

10n-10p

Compound 10n-10p (50%) was obtained by performing synthesis and purification in the same manner as in Preparation Example 10.

$^1$H NMR (400 MHz, $CDCl_3$) δ 7.75 (s, 1H), 7.55 (dd, J=8.3, 1.9 Hz, 1H), 6.78 (d, J=8.3 Hz, 1H), 4.61 (t, J=8.8 Hz, 2H), 4.50-4.41 (m, 4H), 3.22 (t, J=8.7 Hz, 2H), 1.51 (s, 9H).

<Preparation Example 14> Tert-butyl-2-(3,4-dichlorophenyl)-1-(2-(methylthio)pyrimidin-4-yl)-4,6-dihydropyrrolo[3,4-d]imidazole-5(1H)-carboxylate (Compound 12a-12f)

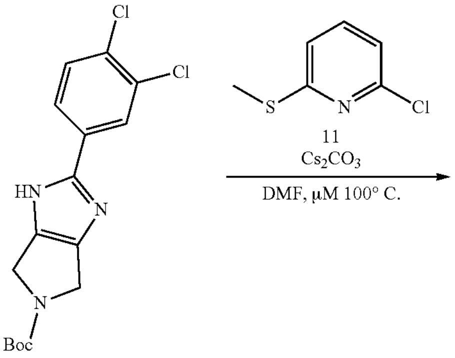

10a-10f

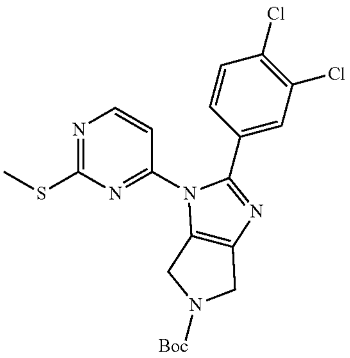

12a-12f

Compound 10a-10f (0.75 mol), Compound 11 (0.75 mmol), and $Cs_2CO_3$ (cesium carbonate, 0.9 mmol) were dissolved in 7.5 ml of N,N-dimethylformamide and the resulting solution was stirred in a microwave at 100° C. for 2 hours. After 2 hours, the reaction mixture was extracted with ethyl acetate (EtOAc) and washed with water and brine. After the product was dried over anhydrous magnesium sulfate ($MgSO_4$) and concentrated, the product was purified by column chromatography on silica gel using the mobile phase of EA:HEX (1:2) to obtain Compound 12a-12f (50%).

$^1$H NMR (400 MHz, $CDCl_3$) δ 8.28 (dd, J=7.6, 5.5 Hz, 1H), 8.13 (d, J=16.5 Hz, 1H), 7.88 (t, J=8.7 Hz, 3H), 7.62-7.53 (m, 3H), 6.42 (d, J=5.5 Hz, 1H), 4.86-4.79 (m, 2H), 4.59 (s, 2H), 2.55 (d, J=3.4 Hz, 3H), 1.54 (s, 9H).

<Preparation Example 15> Tert-butyl-1-(2-(methylthio)pyrimidin-4-yl)-2-(naphthalen-2-yl)-4,6-dihydropyrrolo[3,4-d]imidazole-5(1H)-carboxylate (Compound 12g-12i)

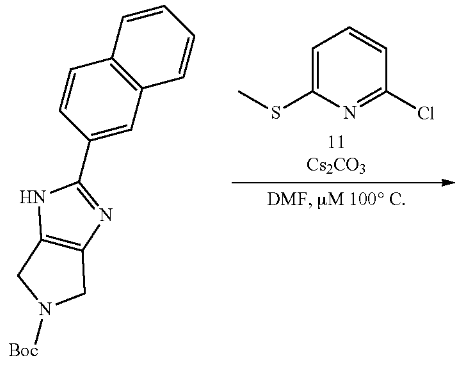

10g-10i

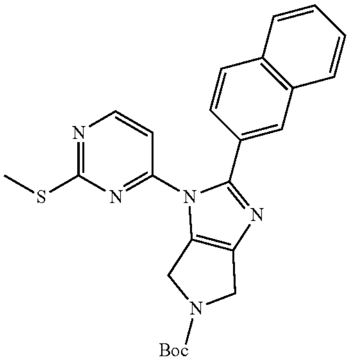

12g-12i

Compound 12g-12i (22%) was obtained by performing synthesis and purification in the same manner as in Preparation Example 14.

$^1$H NMR (400 MHz, $CDCl_3$) δ 8.28 (dd, J=7.6, 5.5 Hz, 1H), 8.13 (d, J=16.5 Hz, 1H), 7.89 (d, J=9.0 Hz, 3H), 7.62-7.53 (m, 2H), 7.53-7.47 (m, 1H), 6.42 (d, J=5.5 Hz, 1H), 4.86-4.79 (m, 2H), 4.59 (s, 2H), 2.55 (d, J=3.4 Hz, 3H), 1.54 (s, 9H).

<Preparation Example 16> Tert-butyl-2-(benzo[d][1,3]dioxol-5-yl)-1-(2-(methylthio)pyrimidin-4-yl)-4,6-dihydropyrrolo[3,4-d]imidazole-5(1H)-carboxylate (Compound 12j-12m)

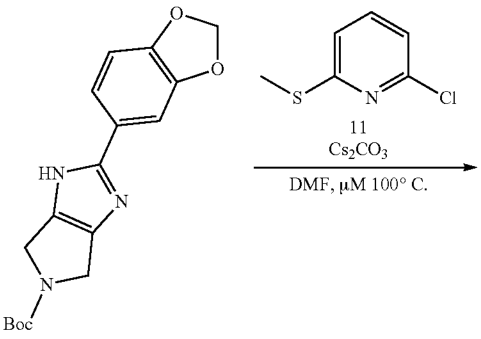

10j-10m

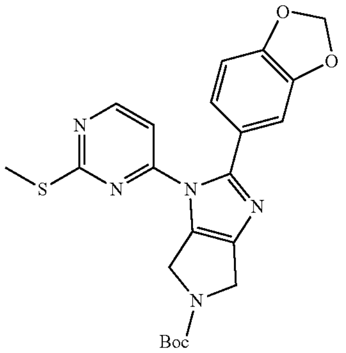

12j-12m

Compound 12j-12m (47%) was obtained by performing synthesis and purification in the same manner as in Preparation Example 14.

$^1$H NMR (400 MHz, $CDCl_3$) δ 8.35 (dd, J=5.5, 1.1 Hz, 1H), 7.00-6.93 (m, 2H), 6.85 (d, J=7.9 Hz, 1H), 6.46 (t, J=5.6 Hz, 1H), 6.04 (s, 2H), 4.83-4.72 (m, 2H), 4.54-4.45 (m, 2H), 2.56 (d, J=2.1 Hz, 3H), 1.52 (d, J=1.8 Hz, 9H).

<Preparation Example 17> Tert-butyl-2-(2,3-dihydrobenzofuran-5-yl)-1-(2-(methylthio)pyrimidin-4-yl)-4,6-dihydropyrrolo[3,4-d]imidazole-5(1H)-carboxylate (Compound 12n-12p)

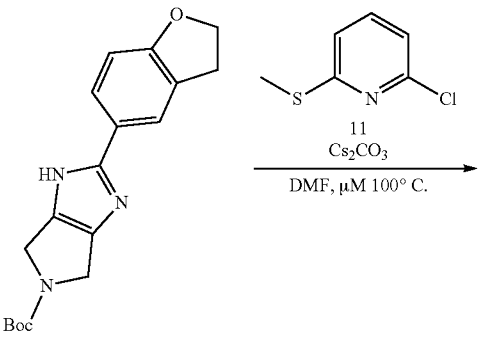

10n-10p

-continued

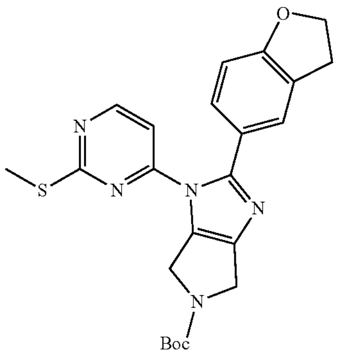

12n-12p

Compound 12n-12p (52%) was obtained by performing synthesis and purification in the same manner as in Preparation Example 14.

$^1$H NMR (400 MHz, $CDCl_3$) δ 8.32 (d, J=5.5 Hz, 1H), 7.38 (s, 1H), 7.19 (d, J=8.3 Hz, 1H), 6.80 (d, J=8.3 Hz, 1H), 6.46 (t, J=5.5 Hz, 1H), 4.82-4.74 (m, 2H), 4.65 (t, J=8.8 Hz, 2H), 4.51 (dd, J=12.7, 9.5 Hz, 2H), 3.24 (t, J=8.8 Hz, 2H), 2.57 (d, J=1.3 Hz, 3H), 1.53 (d, J=1.7 Hz, 9H).

<Preparation Example 18> Tert-butyl-(S)-1-(2-((1-(cyclopropanecarboxyl)piperidin-3-yl)amino)pyrimidin-4-yl)-2-(3,4-dichlorophenyl)-4,6-dihydropyrrolo[3,4-d]imidazole-5(1H)-carboxylate (Compound 14a-14b)

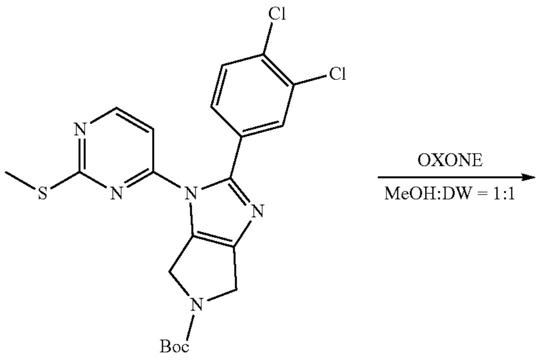

12a-12b

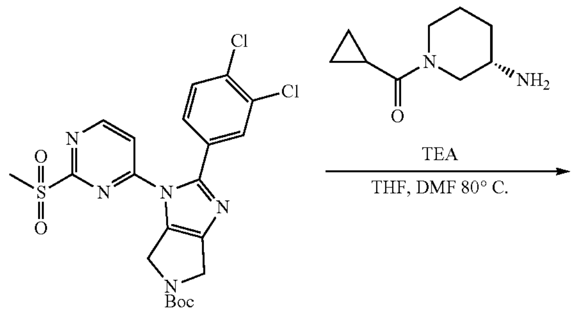

13a-13b

-continued

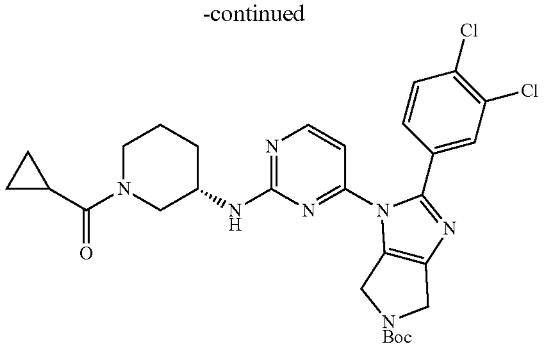

14a-14b

After Compound 12a-12b (0.16 mmol) was dissolved in 2 ml of methanol, potassium peroxomonosulfate (0.8 mmol) dissolved in 2 ml of water was added thereto, and the resulting mixture was stirred at ambient temperature for 2 hours. When Compound 12a-12b disappeared in TLC, methanol was concentrated, and then extraction was performed with ethyl acetate (EtOAc), followed by washing with water and brine. The resulting product was dried over anhydrous magnesium sulfate ($MgSO_4$) and the solvent was concentrated under vacuum to obtain Compound 13a-13b. After (S)-(3-aminopiperidin-1-yl)(cyclopropyl)methanone (0.32 mmol) was dissolved in 1 ml of dimethylformamide, 44.5 μl (0.32 mmol) of triethylamine was added thereto. Thereafter, Compound 13a-13b (0.14 mmol) dissolved in 3 ml of tetrahydrofuran was added thereto, and the resulting mixture was stirred at 80° C. for 24 hours. When Compound 13 disappeared in TLC, tetrahydrofuran was concentrated under vacuum, and then extraction was performed with ethyl acetate (EtOAc), followed by washing with water and brine. After the product was dried over anhydrous magnesium sulfate ($MgSO_4$) and concentrated, the product was purified by column chromatography on silica gel using the mobile phase of EA:HEX (5:1) to obtain Compound 14a-14b (48%).

$^1$H NMR (400 MHz, $CDCl_3$) δ 8.20 (s, 1H), 7.66 (s, 1H), 7.47 (d, J=8.3 Hz, 1H), 7.35-7.27 (m, 1H), 6.13 (d, J=5.4 Hz, 1H), 4.71 (d, J=33.9 Hz, 2H), 4.49 (d, J=25.9 Hz, 2H), 3.75 (d, J=31.6 Hz, 5H), 1.79-1.59 (m, 5H), 1.52 (d, J=2.8 Hz, 9H), 1.01 (s, 2H), 0.77 (s, 2H).

<Preparation Example 19> Tert-butyl-(S)-1-(2-((1-(cyclopropanecarboxyl)piperidin-3-yl)amino)pyrimidin-4-yl)-2-(naphthalen-2-yl)-4,6-dihydropyrrolo[3,4-d]imidazole-5(1H)-carboxylate (Compound 14g)

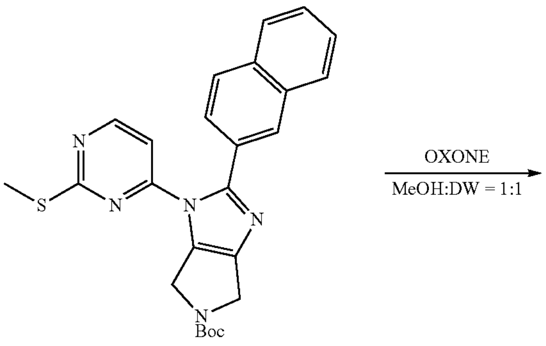

12g

-continued

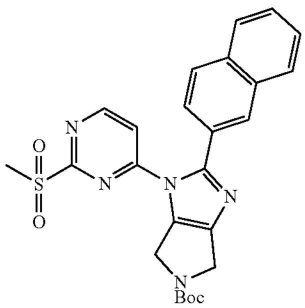

13g

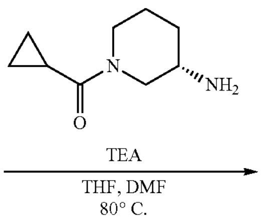

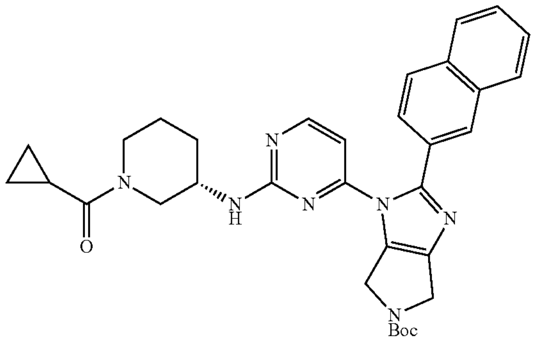

14g

Compound 14g (52%) was obtained by performing synthesis and purification in the same manner as in Preparation Example 18.

$^1$H NMR (400 MHz, $CDCl_3$) δ 8.06 (s, 2H), 7.84 (t, J=7.3 Hz, 3H), 7.58-7.46 (m, 3H), 6.05 (s, 1H), 4.85-4.64 (m, 2H), 4.52 (d, J=27.5 Hz, 2H), 3.96-3.46 (m, 4H), 1.97-1.57 (m, 5H), 1.53 (d, J=2.3 Hz, 9H), 1.03-0.67 (m, 5H).

<Preparation Example 20> Tert-butyl-(S)-2-(benzo[d][1,3]dioxol-5-yl)-1-(2-((1-(cyclopropanecarbonyl)piperidin-3-yl)amino)pyrimidin-4-yl)-4,6-dihydropyrrolo[3,4-d]imidazole-5(1H)-carboxylate (Compound 14j)

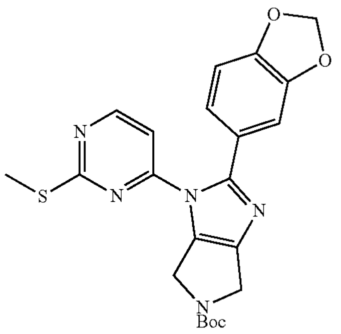

12j

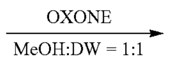

-continued

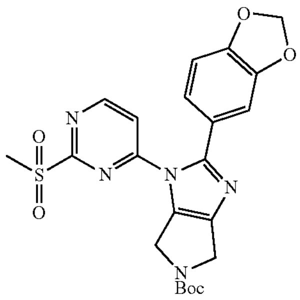

13j

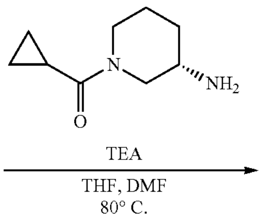

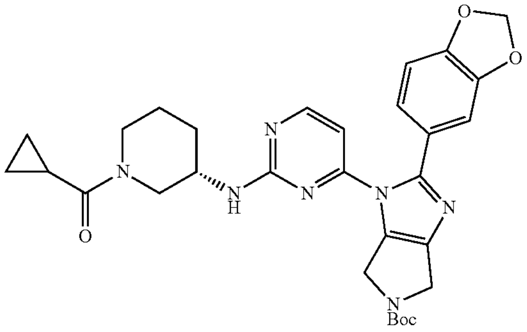

14j

Compound 14j (52%) was obtained by performing synthesis and purification in the same manner as in Preparation Example 18.

$^1$H NMR (400 MHz, $CDCl_3$) δ 8.11 (s, 1H), 6.98-6.88 (m, 2H), 6.81 (d, J=8.0 Hz, 1H), 6.02 (d, J=8.7 Hz, 3H), 4.69 (d, J=27.0 Hz, 2H), 4.46 (d, J=26.1 Hz, 2H), 3.97-3.52 (m, 5H), 1.82-1.56 (m, 5H), 1.50 (d, J=2.4 Hz, 9H), 1.02-0.92 (m, 2H), 0.76 (d, J=3.2 Hz, 2H).

<Preparation Example 21> Tert-butyl-(S)-1-(2-((1-(cyclopropanecarbonyl)piperidin-3-yl)amino)pyrimidin-4-yl)-2-(2,3-dihydrobenzofuran-5-yl)-4,6-dihydropyrrolo[3,4-d]imidazole-5(1H)-carboxylate (Compound 14n)

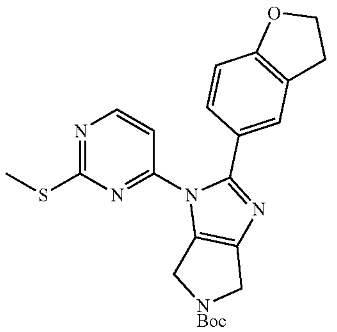

12n

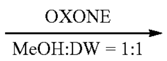

-continued

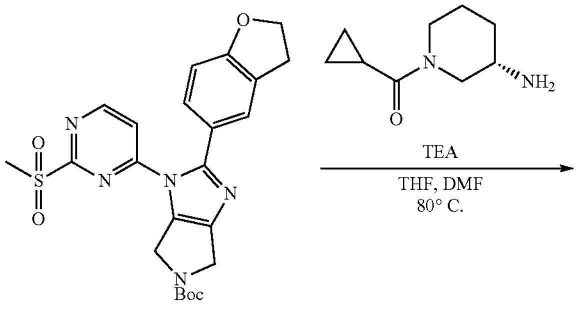

13n

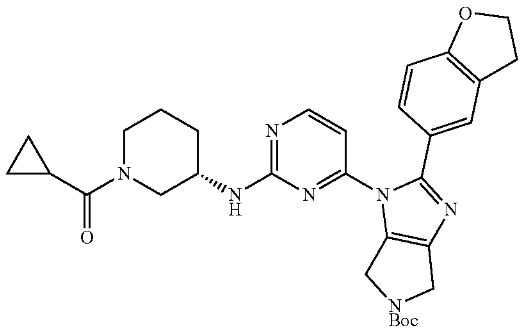

14n

Compound 14n (52%) was obtained by performing synthesis and purification in the same manner as in Preparation Example 18.

$^1$H NMR (400 MHz, $CDCl_3$) δ 8.09 (s, 1H), 7.35 (d, J=8.2 Hz, 1H), 7.17 (s, 1H), 6.76 (d, J=8.3 Hz, 1H), 6.07 (s, 1H), 4.71 (d, J=29.1 Hz, 2H), 4.62 (t, J=8.8 Hz, 2H), 4.47 (d, J=26.7 Hz, 2H), 3.70 (dd, J=91.3, 72.0 Hz, 6H), 3.22 (t, J=8.7 Hz, 2H), 1.80-1.56 (m, 5H), 1.51 (d, J=2.5 Hz, 9H), 1.00 (s, 2H), 0.88 (d, J=6.5 Hz, 2H).

<Preparation Example 22> Tert-butyl-(R)-1-(2-((1-(cyclopropanecarbonyl)pyrrolidin-3-yl)amino)pyrimidin-4-yl)-2-(3,4-dichlorophenyl)-4,6-dihydropyrrolo[3,4-d]imidazole-5(1H)-carboxylate (Compound 14c)

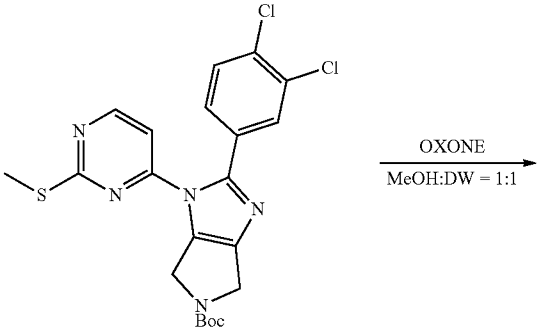

12c

-continued

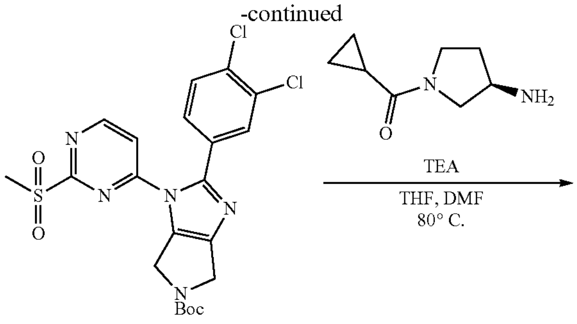

13c

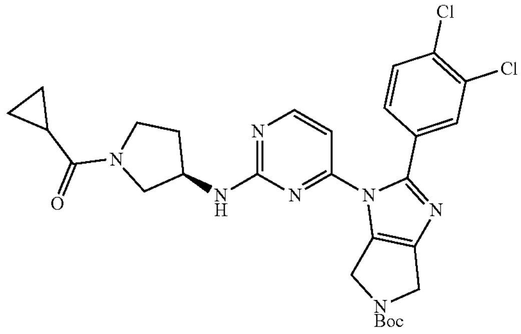

14c

After Compound 12c (0.16 mmol) was dissolved in 2 ml of methanol, potassium peroxomonosulfate (0.8 mmol) dissolved in 2 ml of water was added thereto, and the resulting mixture was stirred at ambient temperature for 2 hours. When Compound 12c disappeared in TLC, methanol was concentrated, and then extraction was performed with ethyl acetate (EtOAc), followed by washing with water and brine. The resulting product was dried over anhydrous magnesium sulfate ($MgSO_4$) and the solvent was concentrated under vacuum to obtain Compound 13c. After (S)-(3-aminopyrrolidin-1-yl)(cyclopropyl)methanone (0.32 mmol) was dissolved in 1 ml of dimethylformamide, 44.5 μl (0.32 mmol) of triethylamine was added thereto. Thereafter, Compound 13c (0.14 mmol) dissolved in 3 ml of tetrahydrofuran was added thereto, and the resulting mixture was stirred at 80° C. for 24 hours. When Compound 13c disappeared in TLC, tetrahydrofuran was concentrated under vacuum, and then extraction was performed with ethyl acetate (EtOAc), followed by washing with water and brine. After the resulting product was dried over anhydrous magnesium sulfate ($MgSO_4$) and concentrated, the product was purified by column chromatography on silica gel using the mobile phase of EA:HEX (10:1) to obtain Compound 14c (38%).

$^1$H NMR (400 MHz, MeOD) δ 8.34-8.26 (m, 1H), 7.76-7.70 (m, 1H), 7.62 (dd, J=8.3, 1.1 Hz, 1H), 7.41 (ddd, J=8.2, 4.0, 2.0 Hz, 1H), 6.31 (d, J=5.2 Hz, 1H), 4.77 (d, J=12.9 Hz, 2H), 4.48 (d, J=2.6 Hz, 2H), 3.96-3.54 (m, 4H), 2.32-2.03 (m, 4H), 1.56 (d, J=2.5 Hz, 9H), 0.94-0.85 (m, 4H).

<Preparation Example 23> Tert-butyl-(R)-1-(2-((1-(cyclopropanecarbonyl)pyrrolidin-3-yl)amino)pyrimidin-4-yl)-2-(naphthalen-2-yl)-4,6-dihydropyrrolo[3,4-d]imidazole-5(1H)-carboxylate (Compound 14h)

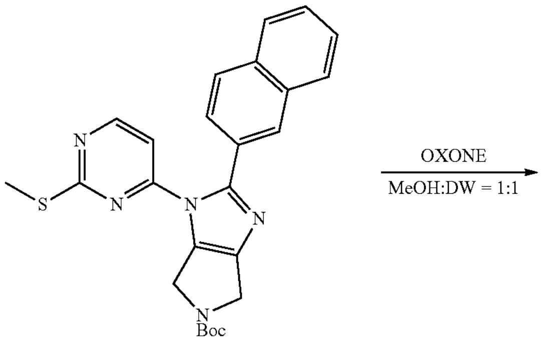

12h

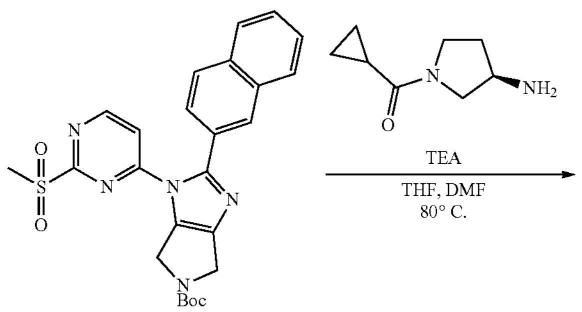

13h

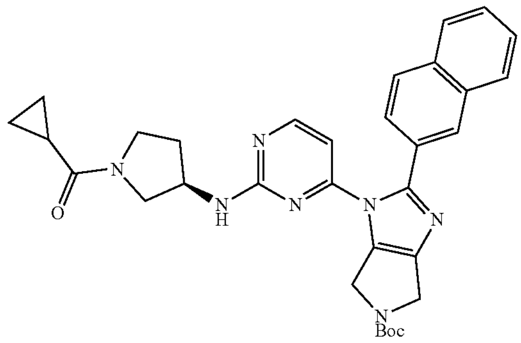

14h

Compound 14h (30%) was obtained by performing synthesis and purification in the same manner as in Preparation Example 22.

$^1$H NMR (400 MHz, $CDCl_3$) δ 8.14-8.00 (m, 2H), 7.85 (d, J=7.9 Hz, 3H), 7.58-7.49 (m, 3H), 6.16-6.03 (m, 1H), 4.77 (d, J=16.4 Hz, 2H), 4.53 (d, J=26.8 Hz, 2H), 3.79-3.50 (m, 4H), 2.18 (d, J=13.6 Hz, 4H), 1.53 (s, 9H), 1.00 (s, 2H), 0.78 (d, J=5.1 Hz, 2H).

<Preparation Example 24> Tert-butyl-(R)-2-(benzo[d][1,3]dioxol-5-yl)-1-(2-((1-(cyclopropanecarbonyl)pyrrolidin-3-yl)amino)pyrimidin-4-yl)-4,6-dihydro-pyrrolo [3,4-d]imidazole-5(1H)-carboxylate (Compound 14k)

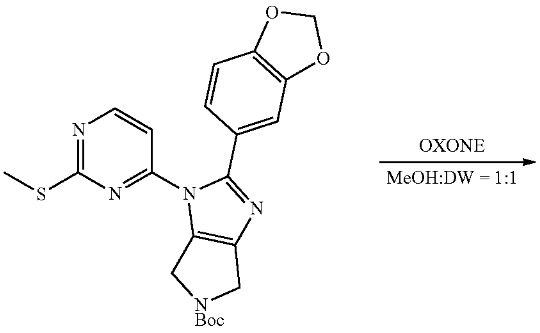

12k

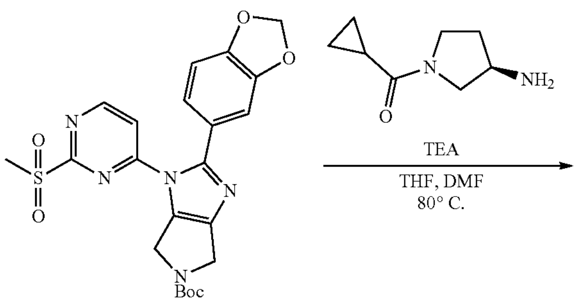

13k

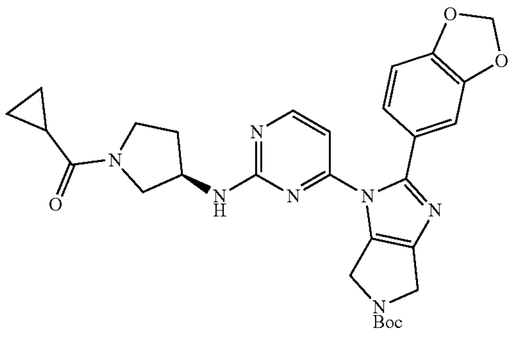

14k

Compound 14k (44%) was obtained by performing synthesis and purification in the same manner as in Preparation Example 22.

$^1$H NMR (400 MHz, $CDCl_3$) δ 8.11 (dd, J=11.3, 5.3 Hz, 1H), 6.98-6.92 (m, 2H), 6.81 (dd, J=8.0, 5.6 Hz, 1H), 6.06-6.00 (m, 3H), 4.71 (dd, J=23.3, 9.4 Hz, 2H), 4.43 (s, 2H), 3.80-3.58 (m, 4H), 2.37-1.95 (m, 4H), 1.52-1.48 (m, 9H), 0.98 (d, J=4.8 Hz, 2H), 0.78-0.74 (m, 2H).

<Preparation Example 25> Tert-butyl-(R)-1-(2-((1-(cyclopropanecarbonyl)pyrrolidin-3-yl)amino)pyrimidin-4-yl)-2-(2,3-dihydrobenzofuran-5-yl)-4,6-dihydropyrrolo[3,4-d]imidazole-5(1H)-carboxylate (Compound 14o)

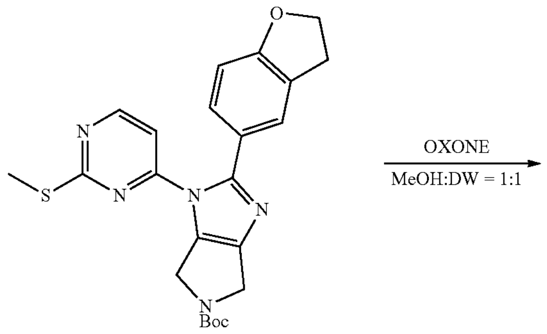

12o

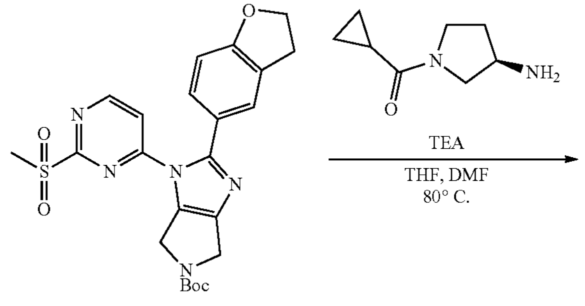

13o

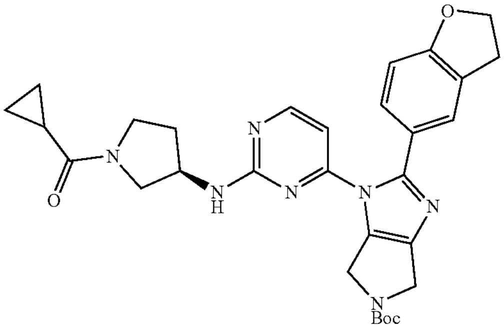

14o

Compound 14o (48%) was obtained by performing synthesis and purification in the same manner as in Preparation Example 22.

$^1H$ NMR (400 MHz, $CDCl_3$) δ 8.09 (dd, J=12.1, 5.2 Hz, 1H), 7.35 (d, J=10.3 Hz, 1H), 7.21-7.14 (m, 1H), 6.77 (dd, J=8.2, 3.7 Hz, 1H), 6.10 (ddd, J=15.8, 12.2, 5.4 Hz, 1H), 4.82-4.68 (m, 2H), 4.63 (d, J=8.8 Hz, 2H), 4.43 (s, 2H), 3.99-3.53 (m, 5H), 3.22 (t, J=8.7 Hz, 2H), 2.39-2.05 (m, 2H), 1.92 (dd, J=12.5, 6.2 Hz, 1H), 1.53-1.48 (m, 9H), 0.77 (dd, J=7.8, 4.7 Hz, 4H).

<Preparation Example 26> Tert-butyl-(S)-1-(2-((1-(cyclopropanecarbonyl)pyrrolidin-3-yl)amino)pyrimidin-4-yl)-2-(3,4-dichlorophenyl)-4,6-dihydropyrrolo[3,4-d]imidazole-5(1H)-carboxylate (Compound 14d)

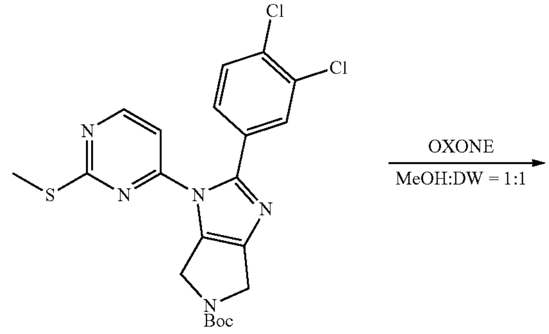

12d

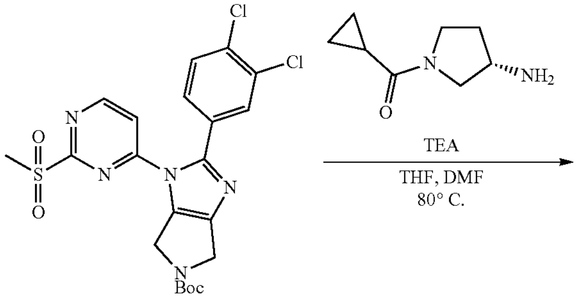

13d

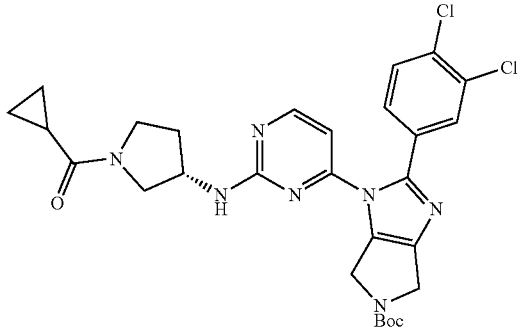

14d

After Compound 12d (0.16 mmol) was dissolved in 2 ml of methanol, potassium peroxomonosulfate (0.8 mmol) dissolved in 2 ml of water was added thereto, and the resulting mixture was stirred at ambient temperature for 2 hours. When Compound 12d disappeared in TLC, methanol was concentrated, and then extraction was performed with ethyl acetate (EtOAc), followed by washing with water and brine. The resulting product was dried over anhydrous magnesium sulfate ($MgSO_4$) and the solvent was concentrated under vacuum to obtain Compound 13d. After (S)-(3-aminopyrrolidin-1-yl)(cyclopropyl)methanone (0.32 mmol) was dissolved in 1 ml of dimethylformamide, 44.5 μl (0.32 mmol) of triethylamine was added thereto. Thereafter, Compound 13d (0.14 mmol) dissolved in 3 ml of tetrahydrofuran was added thereto, and the resulting mixture was stirred at 80° C. for 24 hours. When Compound 13d disappeared in TLC, tetrahydrofuran was concentrated under vacuum, and then extraction was performed with ethyl acetate (EtOAc), followed by washing with water and brine. After the resulting product was dried over anhydrous magnesium sulfate ($MgSO_4$) and concentrated, the product was purified by column chromatography on silica gel using the mobile phase of EA:HEX (10:1) to obtain Compound 14d (32%).

$^1$H NMR (400 MHz, MeOD) δ 8.34-8.26 (m, 1H), 7.76-7.70 (m, 1H), 7.62 (dd, J=8.3, 1.1 Hz, 1H), 7.41 (ddd, J=8.2, 4.0, 2.0 Hz, 1H), 6.31 (d, J=5.2 Hz, 1H), 4.77 (d, J=12.9 Hz, 2H), 4.48 (d, J=2.6 Hz, 2H), 3.89-3.48 (m, 4H), 2.25-2.02 (m, 4H), 1.56 (d, J=2.5 Hz, 9H), 0.96-0.84 (m, 4H).

<Preparation Example 27> Tert-butyl-(S)-1-(2-((1-(cyclopropanecarbonyl)pyrrolidin-3-yl)amino)pyrimidin-4-yl)-2-(naphthalen-2-yl)-4,6-dihydropyrrolo[3,4-d]imidazole-5(1H)-carboxylate (Compound 14i)

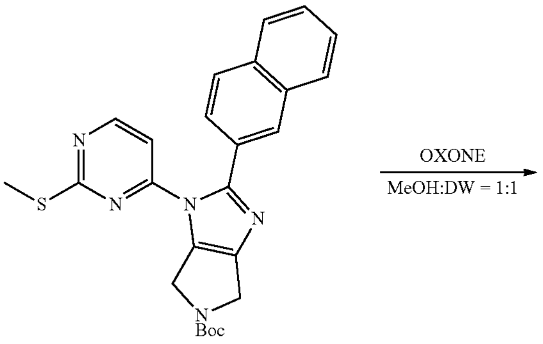

12i

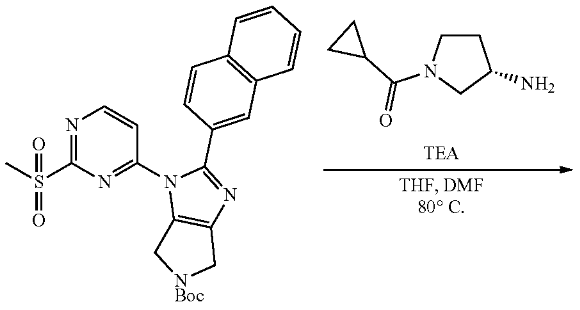

13i

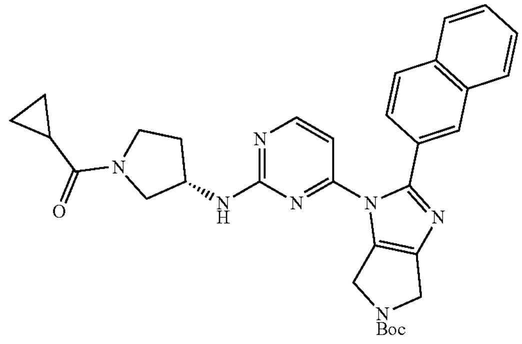

14i

Compound 14i (30%) was obtained by performing synthesis and purification in the same manner as in Preparation Example 26.

$^1$H NMR (400 MHz, $CDCl_3$) δ 8.10-8.02 (m, 2H), 7.85 (d, J=7.2 Hz, 3H), 7.56-7.48 (m, 3H), 6.18-6.02 (m, 1H), 4.77 (d, J=16.3 Hz, 2H), 4.53 (d, J=27.3 Hz, 2H), 3.76-3.55 (m, 4H), 2.28-2.03 (m, 4H), 1.53 (s, 9H), 1.00-0.95 (m, 2H), 0.77 (d, J=4.3 Hz, 2H).

<Preparation Example 28> Tert-butyl-(S)-2-(benzo[d][1,3]dioxol-5-yl)-1-(2-((1-(cyclopropanecarbonyl)pyrrolidin-3-yl)amino)pyrimidin-4-yl)-4,6-dihydropyrrolo[3,4-d]imidazole-5(1H)-carboxylate (Compound 14l)

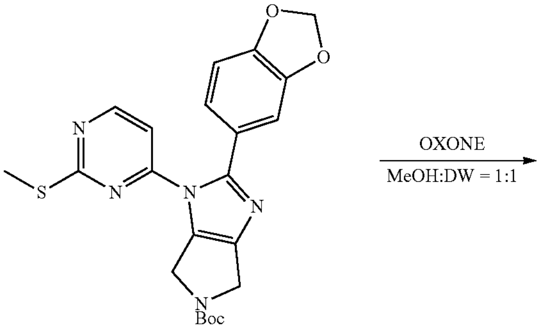

12l

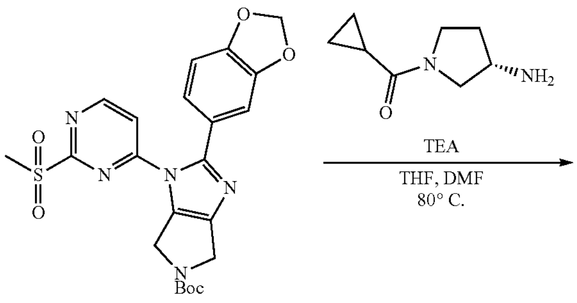

13l

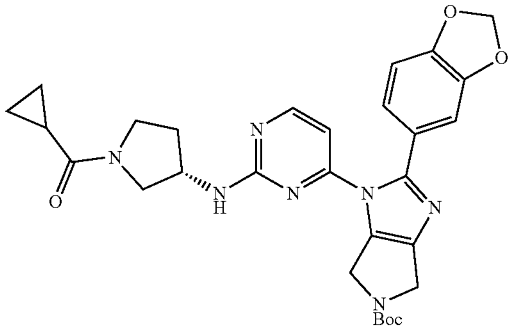

14l

Compound 14l (26%) was obtained by performing synthesis and purification in the same manner as in Preparation Example 26.

$^1$H NMR (400 MHz, $CDCl_3$) δ 8.18-8.09 (m, 1H), 6.97 (ddd, J=8.7, 5.3, 1.5 Hz, 2H), 6.83 (d, J=8.0 Hz, 1H), 6.19-6.06 (m, 1H), 6.02 (d, J=1.1 Hz, 2H), 4.83-4.64 (m, 2H), 4.57-4.42 (m, 2H), 4.03-3.52 (m, 5H), 2.44-2.07 (m, 2H), 1.99-1.81 (m, 1H), 1.52-1.43 (m, 9H), 1.01 (d, J=2.4 Hz, 2H), 0.78 (dd, J=7.5, 4.3 Hz, 2H).

<Preparation Example 29> Tert-butyl-(S)-1-(2-((1-(cyclopropanecarbonyl)pyrrolidin-3-yl)amino)pyrimidin-4-yl)-2-(2,3-dihydrobenzofuran-5-yl)-4,6-dihydropyrrolo[3,4-d]imidazole-5(1H)-carboxylate (Compound 14p)

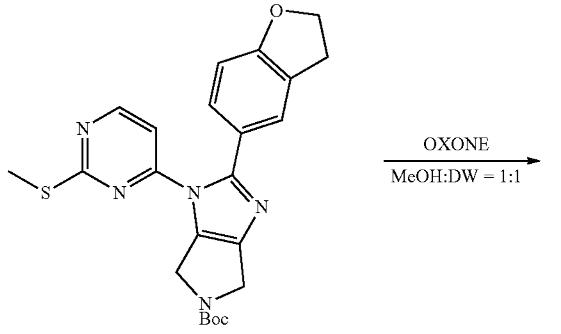

12p

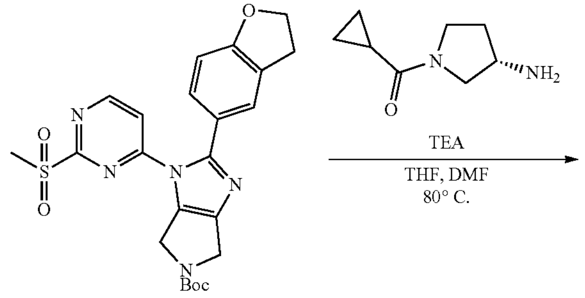

13p

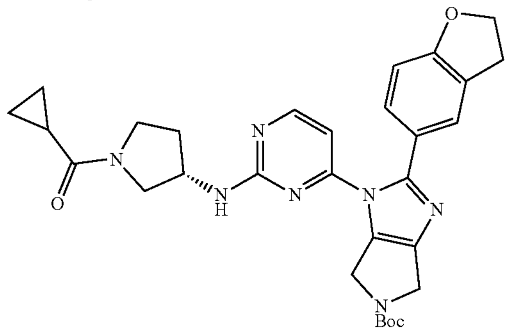

14p

Compound 14p (52%) was obtained by performing synthesis and purification in the same manner as in Preparation Example 26.

$^1$H NMR (400 MHz, $CDCl_3$) δ 8.14-8.03 (m, 1H), 7.35 (d, J=11.0 Hz, 1H), 7.18 (d, J=7.2 Hz, 1H), 6.78 (dd, J=8.2, 3.9 Hz, 1H), 6.10 (ddd, J=15.7, 12.5, 5.5 Hz, 1H), 4.75 (d, J=1.9 Hz, 2H), 4.62 (d, J=8.8 Hz, 2H), 4.44 (s, 2H), 3.85-3.53 (m, 5H), 3.21 (d, J=8.7 Hz, 2H), 2.37-2.07 (m, 2H), 1.93 (dd, J=12.4, 6.0 Hz, 1H), 1.54-1.49 (m, 9H), 1.00 (d, J=2.3 Hz, 2H), 0.79-0.74 (m, 2H).

<Preparation Example 30> Tert-butyl-(S)-1-(2-((1-(cyclobutanecarbonyl)piperidin-3-yl)amino)pyrimidin-4-yl)-2-(3,4-dichlorophenyl)-4,6-dihydropyrrolo[3,4-d]imidazole-5(1H)-carboxylate (Compound 14e)

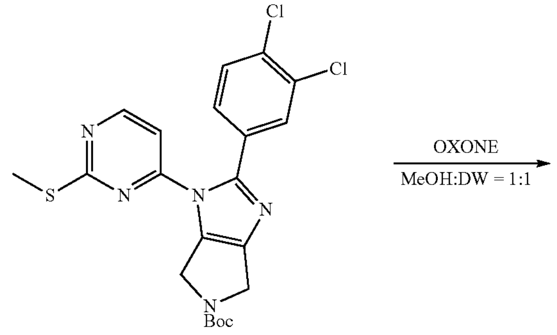

12e

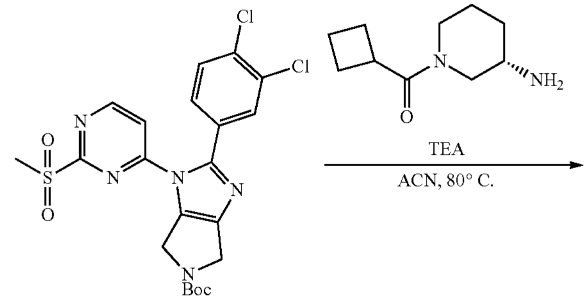

13e

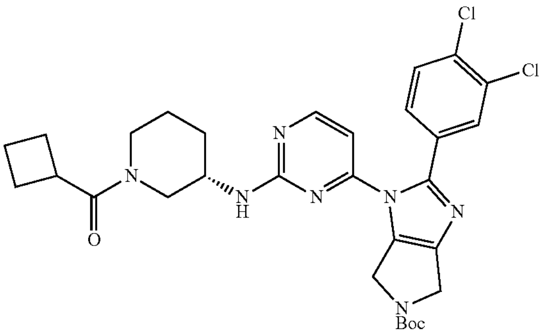

14e

After Compound 12e (0.12 mmol) was dissolved in 1.4 ml of methanol, potassium peroxomonosulfate (0.6 mmol) dissolved in 1.4 ml of water was added thereto, and the resulting mixture was stirred at ambient temperature for 2 hours. When Compound 12e disappeared in TLC, methanol was concentrated, and then extraction was performed with ethyl acetate (EtOAc), followed by washing with water and brine. The resulting product was dried over anhydrous magnesium sulfate ($MgSO_4$) and the solvent was concentrated under vacuum to obtain Compound 13e. After (S)-(3-aminopiperidin-1-yl)(cyclobutyl)methanone (0.2 mmol) was dissolved in 0.5 ml of acetonitrile, 44.5 μl (0.4 mmol) of triethylamine was added thereto. Thereafter, Compound 13e (0.1 mmol) dissolved in 0.5 ml of acetonitrile was added thereto, and the resulting mixture was stirred at 80° C. for 24 hours. When Compound 13e disappeared in TLC, acetonitrile was concentrated under vacuum, and then extraction was performed with ethyl acetate (EtOAc), followed by washing with water and brine. After the resulting product was dried over anhydrous magnesium sulfate ($MgSO_4$) and concentrated, the product was purified by column chromatography on silica gel using the mobile phase of EA HEX (20:1) to obtain Compound 14e (49%).

1H NMR (400 MHz, $CDCl_3$) δ 8.25-8.05 (m, 1H), 7.71-7.62 (m, 1H), 7.47 (dd, J=10.5, 4.8 Hz, 1H), 7.29 (d, J=7.6 Hz, 1H), 6.16 (d, J=5.0 Hz, 1H), 4.70 (dd, J=31.8, 22.8 Hz, 2H), 4.46 (t, J=17.4 Hz, 2H), 3.97-3.54 (m, 3H), 3.42-3.13 (m, 3H), 2.39-2.09 (m, 4H), 2.00-1.62 (m, 6H), 1.50 (d, J=2.4 Hz, 9H).

<Preparation Example 31> Tert-butyl-(S)-1-(2-((1-(cyclopentanecarbonyl)piperidin-3-yl)amino)pyrimidin-4-yl)-2-(3,4-dichlorophenyl)-4,6-dihydropyrrolo[3,4-d]imidazole-5(1H)-carboxylate (14f)

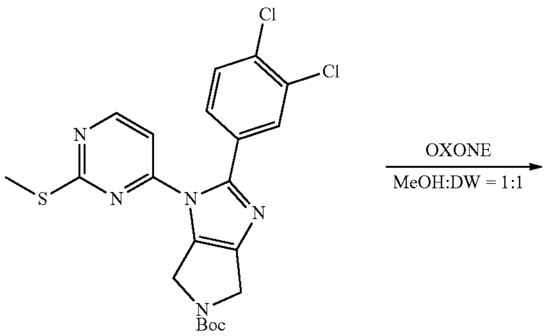

12f

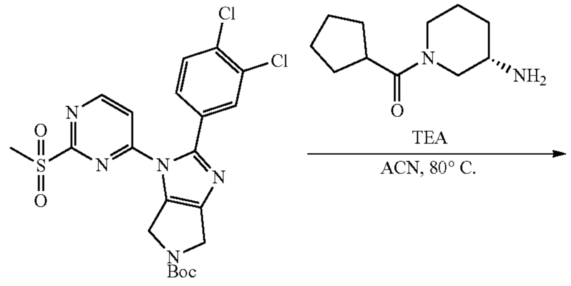

13f

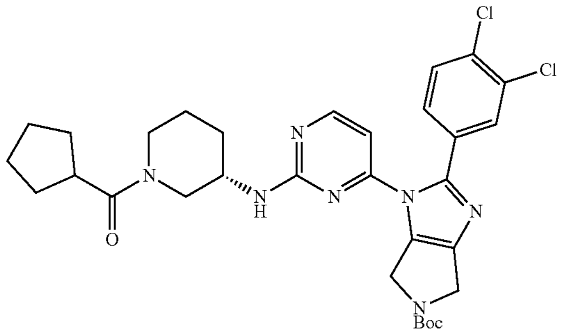

14f

After Compound 12f (0.12 mmol) was dissolved in 1.4 ml of methanol, potassium peroxomonosulfate (0.6 mmol) dissolved in 1.4 ml of water was added thereto, and the resulting mixture was stirred at ambient temperature for 2 hours. When Compound 12e disappeared in TLC, methanol was concentrated, and then extraction was performed with ethyl acetate (EtOAc), followed by washing with water and brine. The resulting product was dried over anhydrous magnesium sulfate ($MgSO_4$) and the solvent was concentrated under vacuum to obtain Compound 13f. After (S)-(3-aminopiperidin-1-yl)(cyclopentyl)methanone (0.2 mmol) was dissolved in 0.5 ml of acetonitrile, 44.5 μl (0.4 mmol) of triethylamine was added thereto. Thereafter, Compound 13f (0.1 mmol) dissolved in 0.5 ml of acetonitrile was added thereto, and the resulting mixture was stirred at 80° C. for 24 hours. When Compound 13e disappeared in TLC, acetonitrile was concentrated under vacuum, and then extraction was performed with ethyl acetate (EtOAc), followed by washing with water and brine. After the resulting product was dried over anhydrous magnesium sulfate ($MgSO_4$) and concentrated, the product was purified by column chromatography on silica gel using the mobile phase of EA HEX (10:1) to obtain Compound 14f (8%).

$^1H$ NMR (400 MHz, $CDCl_3$) δ 8.19 (t, J=30.4 Hz, 1H), 7.68 (s, 1H), 7.51 (dd, J=13.1, 6.2 Hz, 1H), 7.35-7.28 (m, 1H), 6.22 (s, 1H), 4.85-4.66 (m, 2H), 4.49 (d, J=20.4 Hz, 2H), 3.80-3.50 (m, 4H), 2.92 (s, 2H), 1.75 (d, J=38.6 Hz, 12H), 1.51 (d, J=2.5 Hz, 9H).

<Preparation Example 32> Tert-butyl-(S)-2-(benzo[d][1,3]dioxol-5-yl)-1-(2-((1-(cyclobutanecarbonyl)piperidin-3-yl)amino)pyrimidin-4-yl)-4,6-dihydropyrrolo[3,4-d]imidazole-5(1H)-carboxylate (14m)

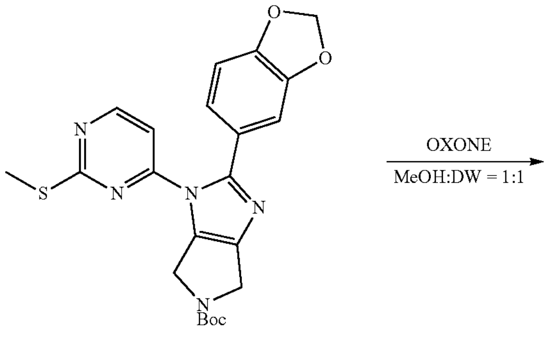

12m

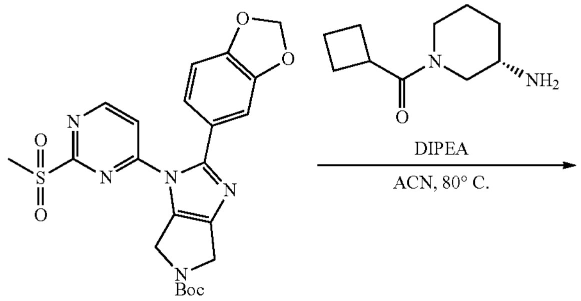

13m

-continued

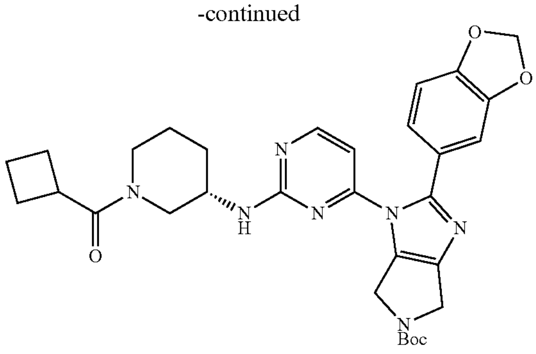

14m

After Compound 12m (0.12 mmol) was dissolved in 1.4 ml of methanol, potassium peroxomonosulfate (0.6 mmol) dissolved in 1.4 ml of water was added thereto, and the resulting mixture was stirred at ambient temperature for 2 hours. When Compound 12e disappeared in TLC, methanol was concentrated, and then extraction was performed with ethyl acetate (EtOAc), followed by washing with water and brine. The resulting product was dried over anhydrous magnesium sulfate ($MgSO_4$) and the solvent was concentrated under vacuum to obtain Compound 13m. After (S)-(3-aminopiperidin-1-yl)(cyclobutyl)methanone (0.2 mmol) was dissolved in 0.5 ml of acetonitrile, 44.5 μl of diisopropylamine (DIPEA) was added thereto. Thereafter, Compound 13m (0.1 mmol) dissolved in 0.5 ml of acetonitrile was added thereto, and the resulting mixture was stirred at 80° C. for 24 hours. When Compound 13e disappeared in TLC, acetonitrile was concentrated under vacuum, and then extraction was performed with ethyl acetate (EtOAc), followed by washing with water and brine. After the resulting product was dried over anhydrous magnesium sulfate ($MgSO_4$) and concentrated, the product was purified by column chromatography on silica gel using the mobile phase of EA HEX (10:1) to obtain Compound 14m (20%).

$^1$H NMR (400 MHz, MeOD) δ 8.28-8.14 (m, 1H), 7.03-6.83 (m, 3H), 6.28 (s, 1H), 6.04 (d, J=2.2 Hz, 2H), 4.80 (s, 2H), 4.47 (d, J=12.3 Hz, 2H), 4.06 (d, J=81.6 Hz, 2H), 3.12-3.02 (m, 1H), 2.94 (s, 1H), 2.15-1.43 (m, 12H).

<Example 1> (S)-(1-(2-((1-(cyclopropanecarbonyl)piperidin-3-yl)amino)pyrimidin-4-yl)-2-(3,4-dichlorophenyl)-4,6-dihydropyrrolo[3,4-d]imidazol-5(1H)-yl)(4-hydroxypiperidin-1-yl)methanone (Compound 16a)

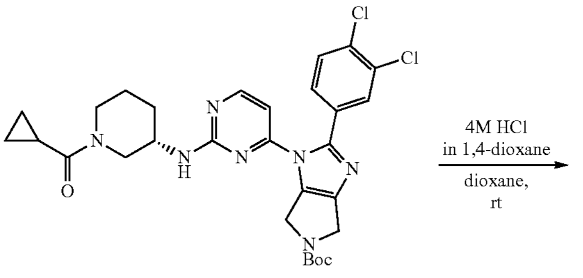

14a

-continued

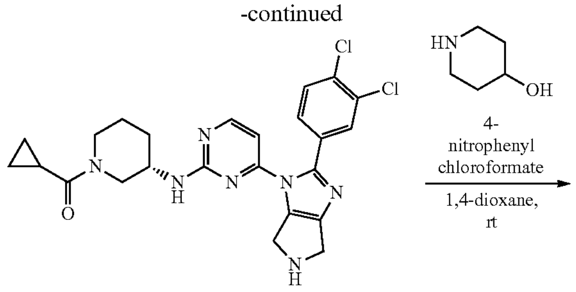

15a

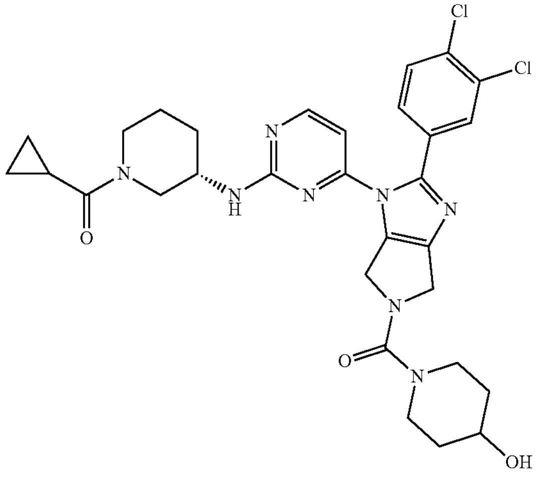

16a

After Compound 14a (0.05 mmol) was dissolved in 0.5 ml of 1,4-dioxane, the resulting solution was treated with 0.25 ml of 4 M HCl in 1,4-dioxane, and then stirred at ambient temperature for 1 hour and 30 minutes. When Compound 14a disappeared in TLC, 1,4-dioxane was concentrated under vacuum, and then Compound 15a was obtained. After Compound 15a (0.044 mmol) was dissolved in 0.44 ml of 1,4-dioxane, the resulting solution was treated with 4-nitrophenyl chloroformate (0.044 mmol) and 0.22 ml of dimethylformamide and the resulting product was stirred at ambient temperature for 1 hour. When Compound 15a disappeared and an intermediate was formed, the intermediate was treated with 4-piperidinol (0.22 mmol) and the resulting product was stirred at ambient temperature for 48 hours. When the intermediate disappeared in TLC, 1,4-dioxane was concentrated under vacuum, and then extraction was performed with ethyl acetate (EtOAc), followed by washing with water and brine. After the product was dried over anhydrous magnesium sulfate ($MgSO_4$) and the solvent was concentrated under vacuum, the product was purified by column chromatography on silica gel using the mobile phase of MC:MeOH (10:1) to obtain Compound 16a (16%).

1H NMR (400 MHz, MeOD) δ 8.27 (dd, J=17.3, 5.0 Hz, 1H), 7.70 (d, J=1.9 Hz, 1H), 7.60 (d, J=8.2 Hz, 1H), 7.38 (s, 1H), 6.29 (s, 1H), 4.95 (s, 2H), 4.58 (t, J=11.4 Hz, 2H), 4.35 (s, 1H), 4.10 (dd, J=14.3, 7.1 Hz, 1H), 3.82 (ddd, J=12.9, 8.6, 3.9 Hz, 1H), 3.71 (d, J=13.7 Hz, 2H), 3.45 (d, J=28.8 Hz, 1H), 3.00 (dd, J=66.0, 53.2 Hz, 4H), 1.90 (dd, J=42.4, 32.4 Hz, 5H), 1.55 (td, J=12.9, 3.6 Hz, 4H), 0.83 (dd, J=32.6, 25.9 Hz, 4H).

<Example 2> (S)-1-(2-((1-(cyclopropanecarbonyl) piperidin-3-yl)amino)pyrimidin-4-yl)-2-(3,4-dichlorophenyl)-4,6-dihydropyrrolo[3,4-d]imidazole-5 (1H)-carboxamide (Compound 16b)

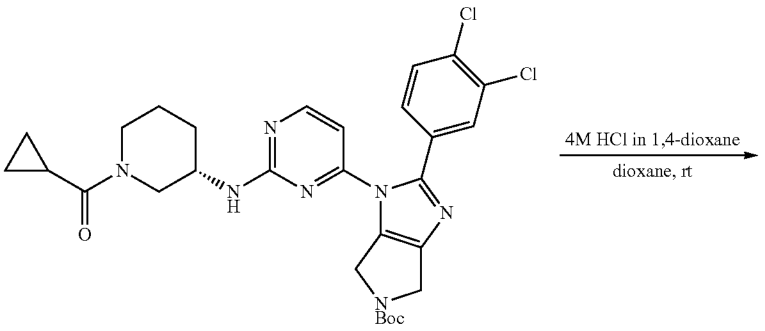

14b

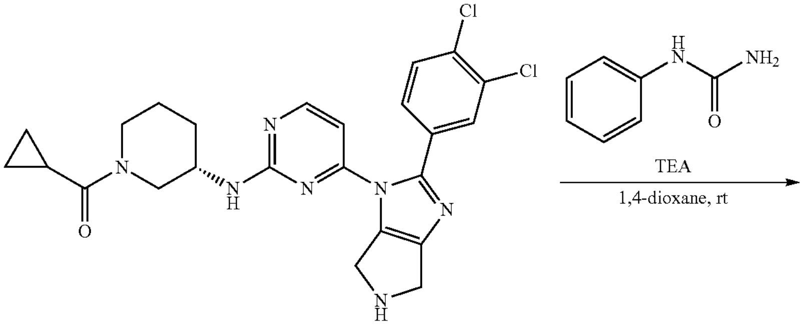

15b

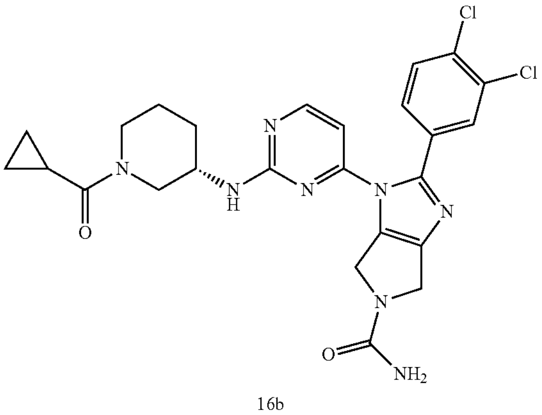

16b

After Compound 14b (0.05 mol) was dissolved in 0.5 ml of 1,4-dioxane, the resulting solution was treated with 0.25 ml of 4 M HCl in 1,4-dioxane, and then stirred at ambient temperature for 1 hour and 30 minutes. When Compound 14b disappeared in TLC, 1,4-dioxane was concentrated under vacuum, and then Compound 15a was obtained. After Compound 15b (0.048 mol) was dissolved in 0.48 ml of 1,4-dioxane, phenyl carbamate (0.048 mmol) and triethylamine (0.048 mmol) were added thereto, and the resulting mixture was stirred at ambient temperature for 24 hours. When Compound 15b disappeared in TLC, 1,4-dioxane was concentrated under vacuum, and then extraction was performed with ethyl acetate (EtOAc), followed by washing with water and brine. After the product was dried over anhydrous magnesium sulfate ($MgSO_4$) and the solvent was concentrated under vacuum, the product was purified by column chromatography on silica gel using the mobile phase of MC:MeOH (10:1) to obtain Compound 16b (31%).

$^1$H NMR (400 MHz, MeOD) δ 8.36-8.23 (m, 1H), 7.69 (s, 1H), 7.59 (d, J=8.2 Hz, 1H), 7.37 (t, J=6.3 Hz, 1H), 6.33 (d, J=75.5 Hz, 1H), 4.76 (s, 2H), 4.49 (dd, J=11.6, 8.5 Hz, 2H), 4.06 (d, J=60.6 Hz, 2H), 3.40-3.05 (m, 5H), 2.10-1.40 (m, 5H), 0.96-0.53 (m, 4H).

<Example 3> (R)-1-(2-((1-(cyclopropanecarbonyl) pyrrolidin-3-yl)amino)pyrimidin-4-yl)-2-(3,4-dichlorophenyl)-4,6-dihydropyrrolo[3,4-d]imidazole-5 (1H)-carboxamide (Compound 16c)
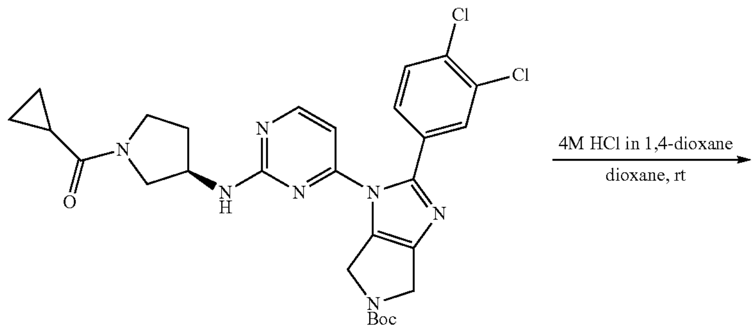
14c
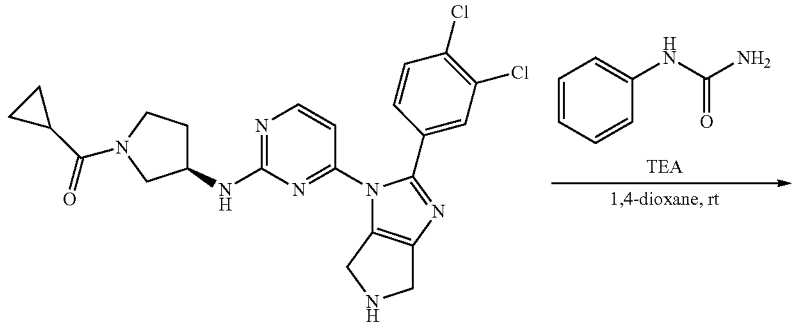
15c
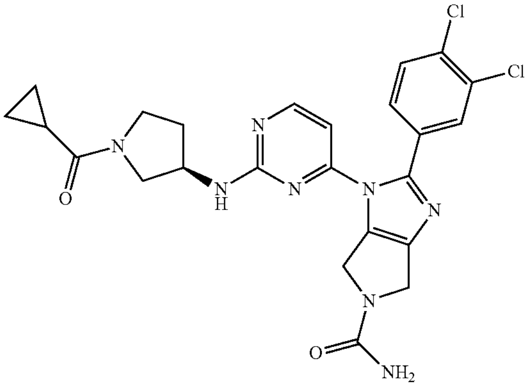
16c Compound 16c (21%) was obtained by performing synthesis and purification in the same manner as in Example 2.

1H NMR (400 MHz, MeOD) δ 8.29 (dd, J=10.5, 5.3 Hz, 1H), 7.72 (t, J=1.8 Hz, 1H), 7.61 (dd, J=8.3, 2.0 Hz, 1H), 7.42-7.38 (m, 1H), 6.30 (s, 1H), 4.78 (d, J=3.0 Hz, 2H), 4.50 (s, 2H), 3.90-3.42 (m, 4H), 2.30-1.71 (m, 4H), 0.87 (ddd, J=10.2, 7.3, 3.4 Hz, 4H).

<Example 4> (S)-1-(2-((1-(cyclopropanecarbonyl)pyrrolidin-3-yl)amino)pyrimidin-4-yl)-2-(3,4-dichlorophenyl)-4,6-dihydropyrrolo[3,4-d]imidazole-5(1H)-carboxamide (Compound 16d)

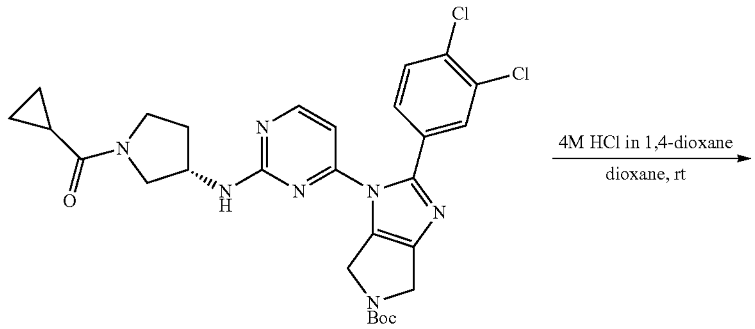

14d

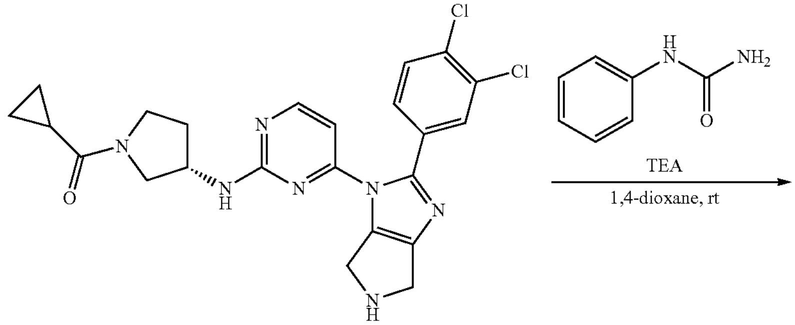

15d

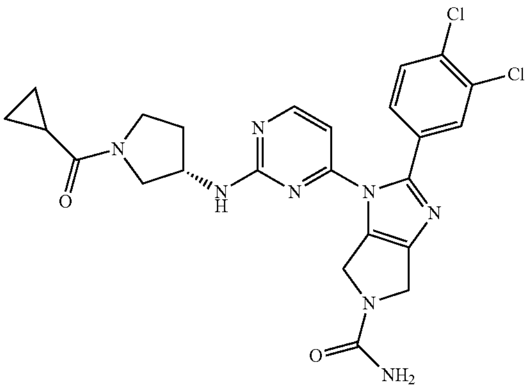

16d

Compound 16d (35%) was obtained by performing synthesis and purification in the same manner as in Example 2.

1H NMR (400 MHz, MeOD) δ 8.29 (dd, J=10.6, 5.3 Hz, 1H), 7.72 (t, J=1.8 Hz, 1H), 7.61 (dd, J=8.3, 2.0 Hz, 1H), 7.42-7.37 (m, 1H), 6.31 (s, 1H), 4.77 (d, J=2.9 Hz, 2H), 4.50 (s, 2H), 3.92-3.46 (m, 4H), 2.30-1.68 (m, 4H), 0.93-0.81 (m, 4H).

<Example 2> (S)-1-(2-((1-(cyclobutanecarbonyl)piperidin-3-yl)amino)pyrimidin-4-yl)-2-(3,4-dichlorophenyl)-4,6-dihydropyrrolo[3,4-d]imidazole-5(1H)-carboxamide (Compound 16e)
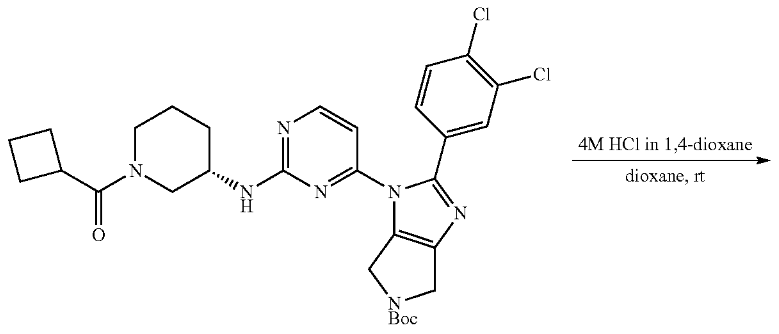
14e
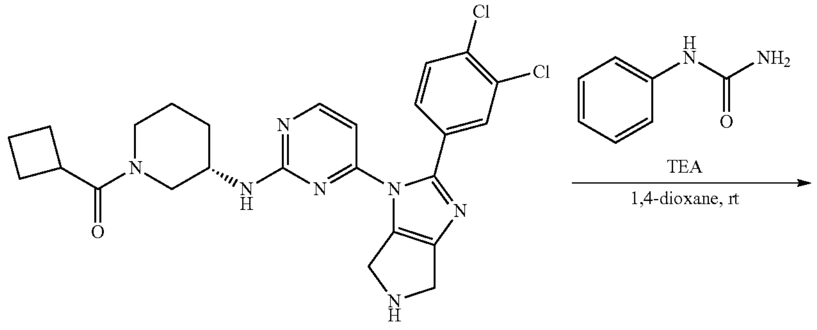
15e
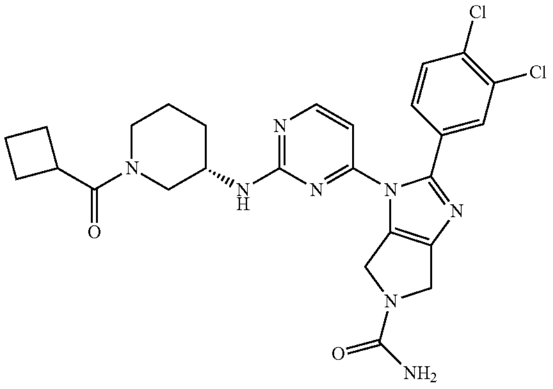
16e
Compound 16e (24%) was obtained by performing synthesis and purification in the same manner as in Example 2.
1H NMR (400 MHz, MeOD) δ 8.40-8.22 (m, 1H), 7.71 (d, J=15.5 Hz, 1H), 7.61 (dd, J=8.3, 4.8 Hz, 1H), 7.43-7.35 (m, 1H), 6.39 (d, J=97.2 Hz, 1H), 4.81 (s, 2H), 4.50 (dd, J=12.3, 2.9 Hz, 2H), 3.68 (s, 1H), 3.53-3.39 (m, 1H), 3.03 (d, J=16.4 Hz, 1H), 2.91 (dd, J=18.5, 8.5 Hz, 1H), 2.42-2.17 (m, 4H), 2.12-1.98 (m, 2H), 1.91-1.71 (m, 3H), 1.66-1.41 (m, 3H).

<Example 6> (S)-1-(2-((1-(cyclopentanecarbonyl) piperidin-3-yl)amin)pyrimidin-4-yl)-2-(3,4-dichloro-phenyl)-4,6-dihydropyrrolo[3,4-d]imidazole-5(1H)-carboxamide (Compound 16f)
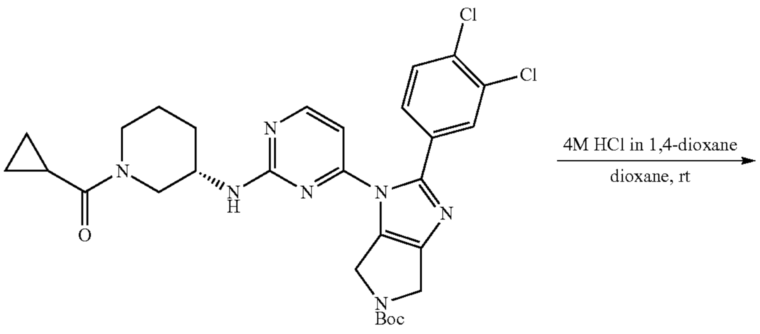
14g
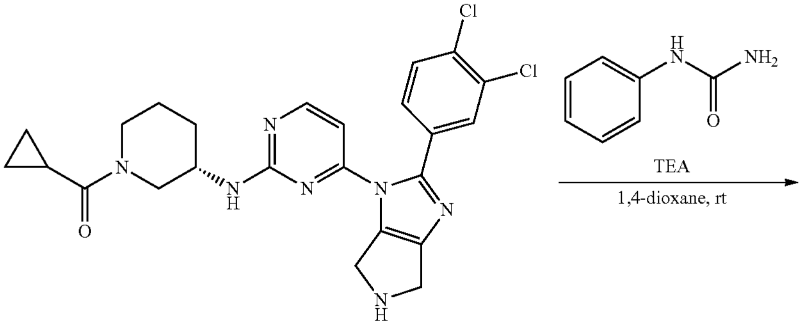
15g
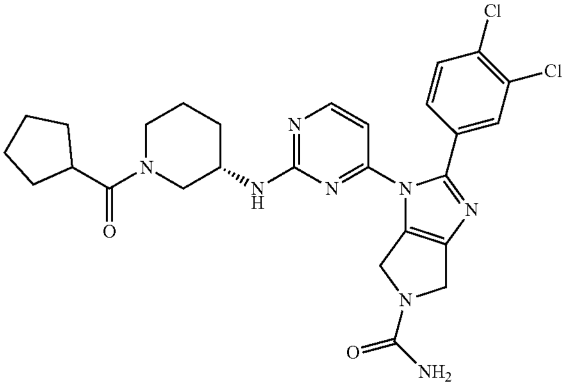
16f
Compound 16f (680%) was obtained by performing synthesis and purification in the same manner as in Example 2.
1H NMR (400 MHz, MeOD) δ 8.38-8.24 (m, 1H), 7.71 (d, J=10.9 Hz, 1H), 7.60 (d, J=8.3 Hz, 1H), 7.42-7.34 (m, 1H), 6.36 (d, J=86.1 Hz, 1H), 4.82 (s, 2H), 4.52 (d, J=9.3 Hz, 2H), 4.21 (s, 1H), 3.97 (d, J=35.3 Hz, 1H), 3.26-3.04 (m, 2H), 2.87 (s, 2H), 2.06-1.56 (m, 12H).

<Example 7> (S)-1-(2-((1-(cyclopropanecarbonyl)piperidin-3-yl)amino)pyrimidin-4-yl)-2-(naphthalen-2-yl)-4,6-dihydropyrrolo[3,4-d]imidazole-5(1H)-carboxamide (Compound 16g)
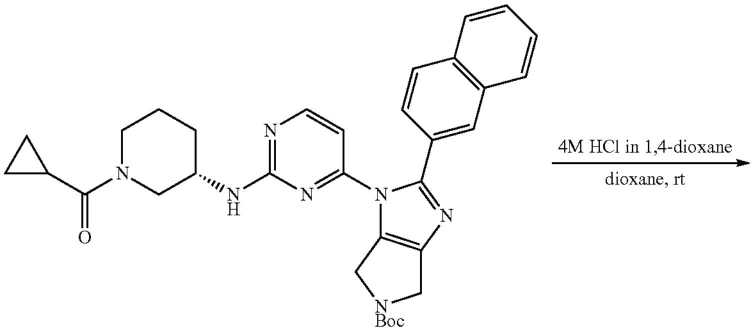
14g
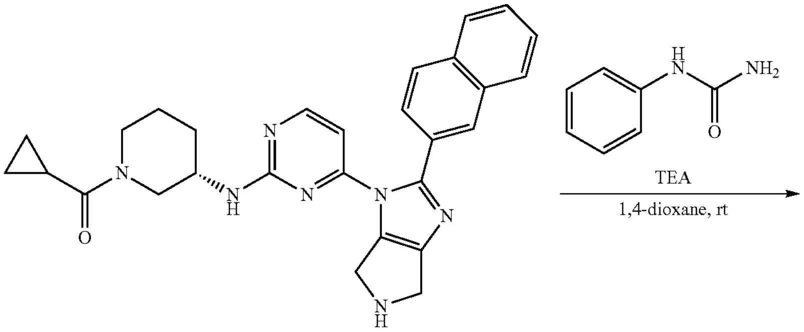
15g
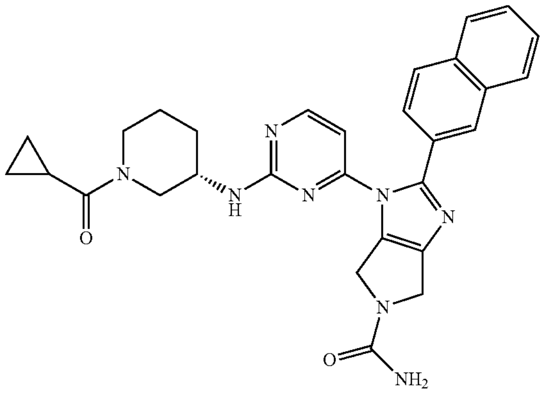
16g
Compound 16g (31%) was obtained by performing synthesis and purification in the same manner as in Example 2.
$^1$H NMR (400 MHz, MeOD) δ 8.29-8.05 (m, 2H), 7.92 (s, 3H), 7.65-7.39 (m, 3H), 6.26 (d, J=102.0 Hz, 1H), 4.69 (d, J=17.1 Hz, 2H), 4.63-4.48 (m, 2H), 4.19-3.72 (m, 2H), 3.29-2.31 (m, 3H), 2.17-1.43 (m, 5H), 0.90 (dt, J=73.7, 30.3 Hz, 4H).

<Example 8> (R)-1-(2-((1-(cyclopropanecarbonyl)pyrrolidin-3-yl)amino)pyrimidin-4-yl)-2-(naphthalen-2-yl)-4,6-dihydropyrrolo[3,4-d]imidazole-5(1H)-carboxamide (Compound 16h)
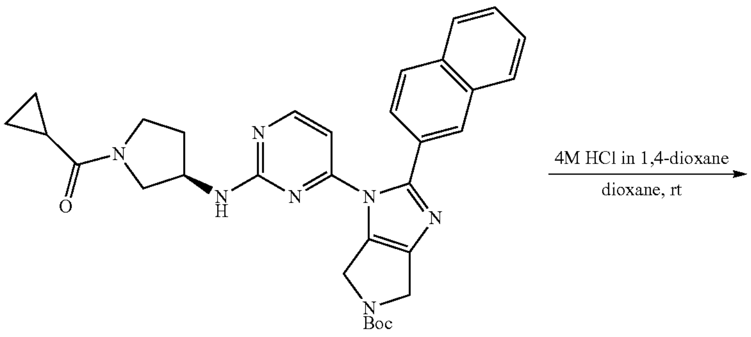
14h
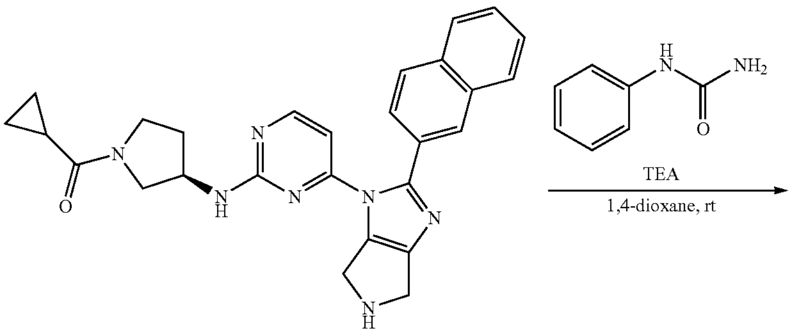
15h
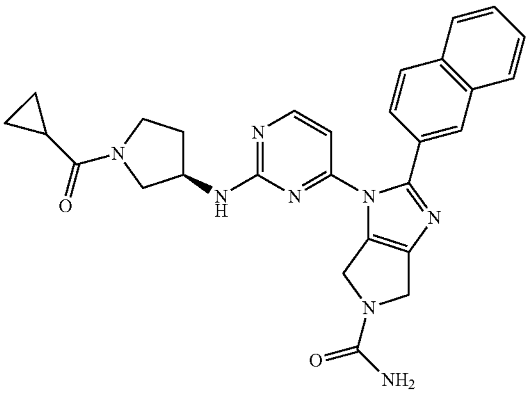
16h
Compound 16h (37%) was obtained by performing synthesis and purification in the same manner as in Example 2.
1H NMR (400 MHz, MeOD) δ 8.26-8.12 (m, 1H), 8.06 (d, J=3.9 Hz, 1H), 7.96-7.85 (m, 3H), 7.62-7.46 (m, 3H), 6.24 (s, 1H), 4.82 (d, J=2.4 Hz, 2H), 4.53 (t, J=3.0 Hz, 2H), 3.99-3.41 (m, 4H), 1.86 (dt, J=102.9, 33.3 Hz, 4H), 0.96-0.70 (m, 4H).

<Example 9> (S)-1-(2-((1-(cyclopropanecarbonyl) pyrrolidin-3-yl)amino)pyrimidin-4-yl)-2-(3,4-dichlorophenyl)-4,6-dihydropyrrolo[3,4-d]imidazole-5 (1H)-carboxamide (Compound 16i)
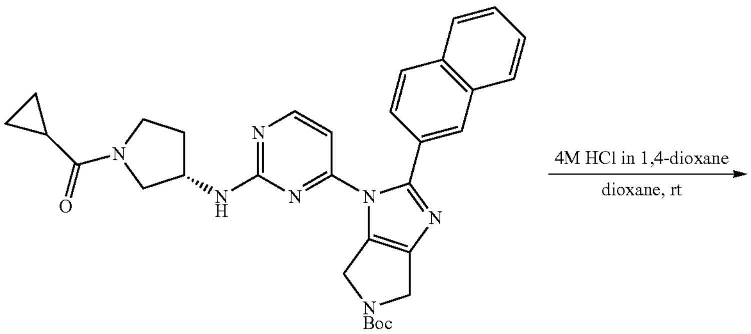
14i
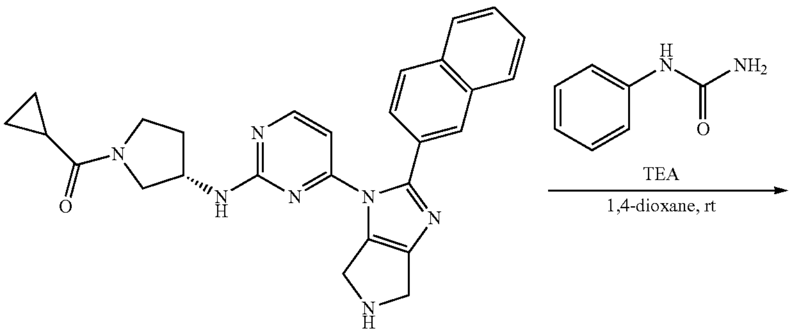
15i
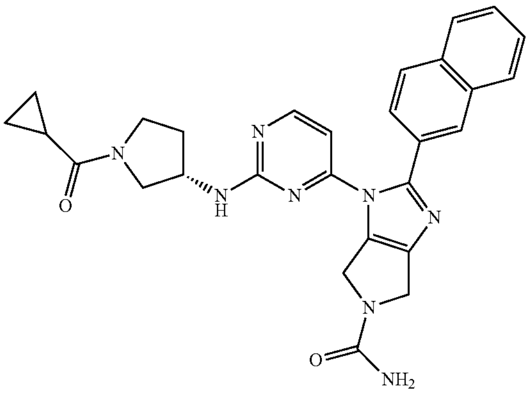
16i
Compound 16i (27%) was obtained by performing synthesis and purification in the same manner as in Example 2.
1H NMR (400 MHz, MeOD) δ 8.25-8.13 (m, 1H), 8.09-8.04 (m, 1H), 7.97-7.86 (m, 3H), 7.64-7.47 (m, 3H), 6.24 (s, 1H), 4.82 (d, J=2.4 Hz, 2H), 4.53 (t, J=2.9 Hz, 2H), 3.91-3.40 (m, 4H), 2.14-1.50 (m, 4H), 0.93-0.76 (m, 4H).

<Example 10> (S)-2-(benzo[d][1,3]dioxol-5-yl)-1-(2-((1-(cyclopropanecarbonyl)piperidin-3-yl)amino)pyrimidin-4-yl)-4,6-dihydropyrrolo[3,4-d]imidazole-5(1H)-carboxamide (Compound 16j)
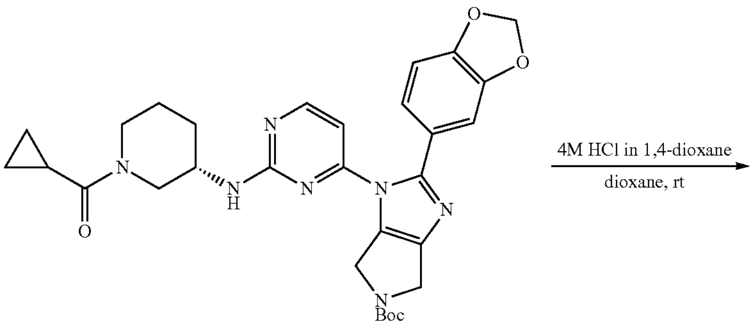
14j
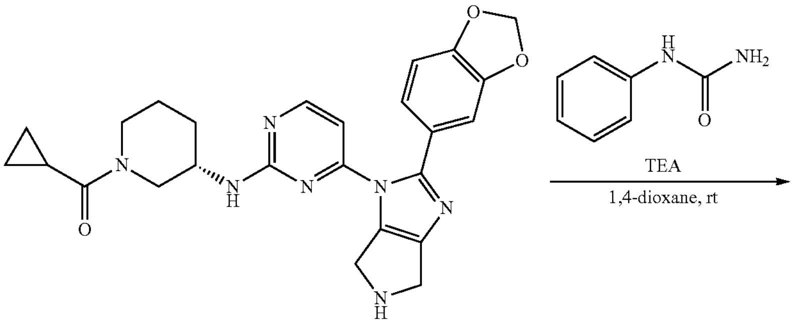
15j
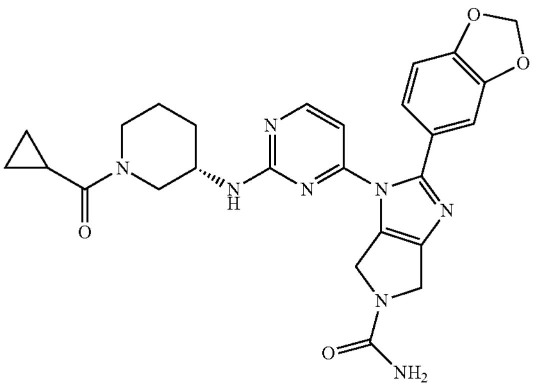
16j
Compound 16j (47%) was obtained by performing synthesis and purification in the same manner as in Example 2.
1H NMR (400 MHz, MeOD) δ 8.28-8.11 (m, 1H), 6.92 (dt, J=20.5, 4.7 Hz, 3H), 6.34-5.99 (m, 3H), 4.76 (s, 2H), 4.47 (s, 2H), 3.98 (ddd, J=139.3, 60.2, 35.9 Hz, 3H), 2.14-1.45 (m, 7H), 0.92-0.68 (m, 4H).

<Example 11> (R)-2-(benzo[d][1,3]dioxol-5-yl)-1-(2-((1-(cyclopropanecarbonyl)pyrrolidin-3-yl)amino)pyrimidin-4-yl)-4,6-dihydropyrrolo[3,4-d]imidazole-5(1H)-carboxamide (Compound 16k)
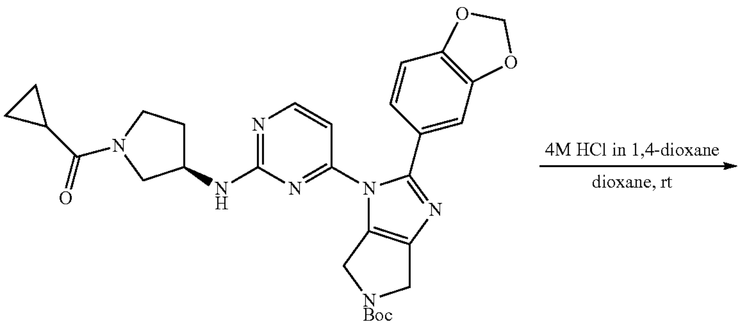
14k
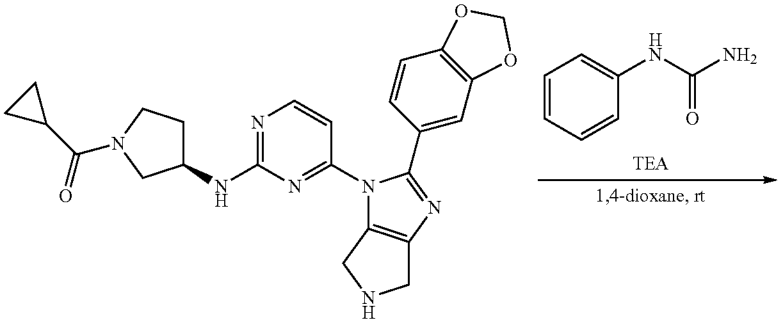
15k
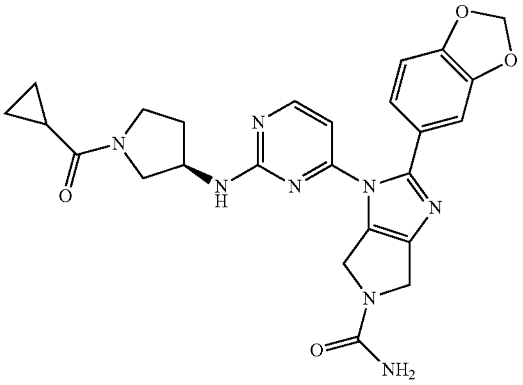
16k
Compound 16k (13%) was obtained by performing synthesis and purification in the same manner as in Example 2.
1H NMR (400 MHz, MeOD) δ 8.21 (dd, J=11.0, 5.4 Hz, 1H), 6.97 (tt, J=3.1, 1.4 Hz, 2H), 6.90 (d, J=8.5 Hz, 1H), 6.18 (s, 1H), 6.04 (dd, J=2.5, 1.3 Hz, 2H), 4.78 (s, 2H), 4.49 (d, J=3.0 Hz, 2H), 3.93-3.39 (m, 5H), 2.40-1.73 (m, 3H), 0.87 (dddd, J=12.5, 9.8, 5.8, 2.2 Hz, 4H).

<Example 12> (S)-2-(benzo[d][1,3]dioxol-5-yl)-1-(2-((1-(cyclopropanecarbonyl)pyrrolidin-3-yl)amino)pyrimidin-4-yl)-4,6-dihydropyrrolo[3,4-d]imidazole-5(1H)-carboxamide (Compound 16l)
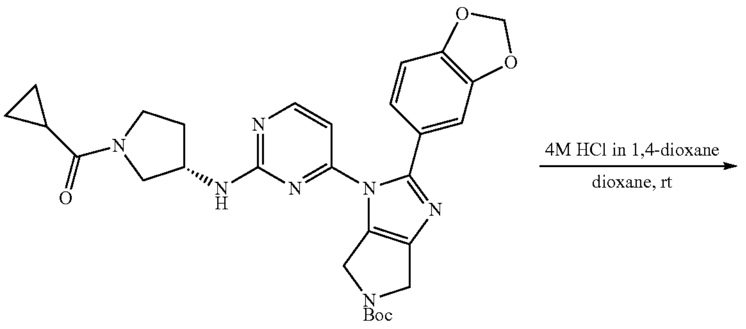
14l
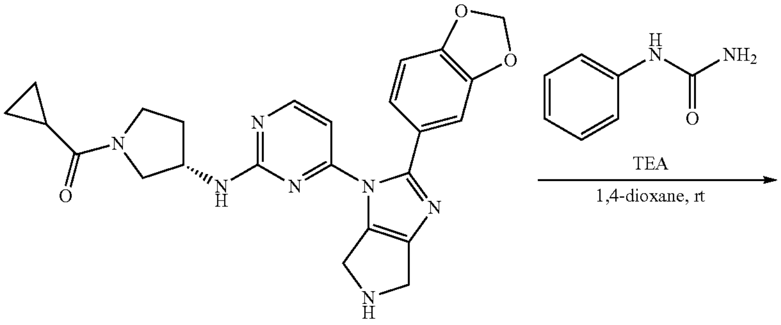
15l
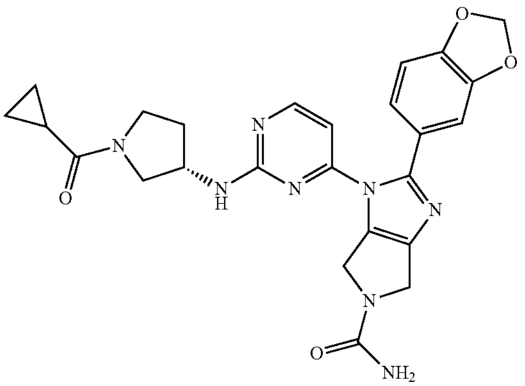
16l
Compound 16l (340%) was obtained by performing synthesis and purification in the same manner as in Example 2.
1H NMR (400 MHz, MeOD) δ 8.21 (dd, J=11.0, 5.4 Hz, 1H), 7.01-6.95 (m, 2H), 6.90 (d, J=8.5 Hz, 1H), 6.21 (d, J=29.0 Hz, 1H), 6.07-6.02 (m, 2H), 4.78 (s, 2H), 4.48 (t, J=3.0 Hz, 2H), 4.35 (s, 1H), 4.02-3.73 (m, 2H), 3.61-3.41 (m, 2H), 2.36-2.05 (m, 2H), 1.80 (dddd, J=28.7, 12.7, 7.9, 4.7 Hz, 1H), 0.92-0.77 (m, 4H).

<Example 13> (S)-2-(benzo[d][1,3]dioxol-5-yl)-1-(2-((1-(cyclobutanecarbonyl)piperidin-3-yl)amino) pyrimidin-4-yl)-4,6-dihydropyrrolo[3,4-d]imidazole-5(1H)-carboxamide (Compound 16m)
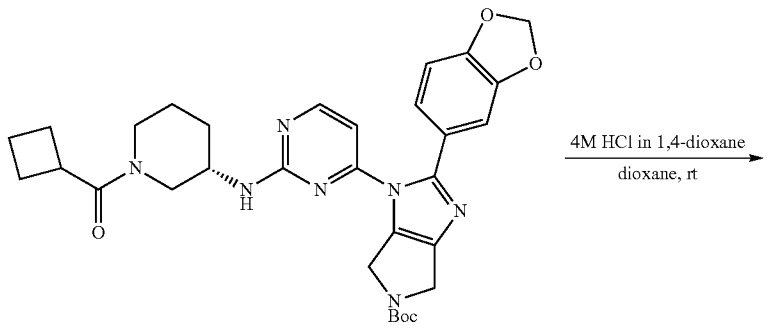
14m
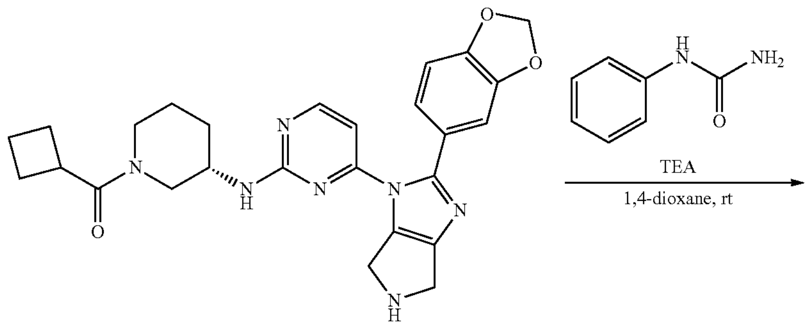
15m
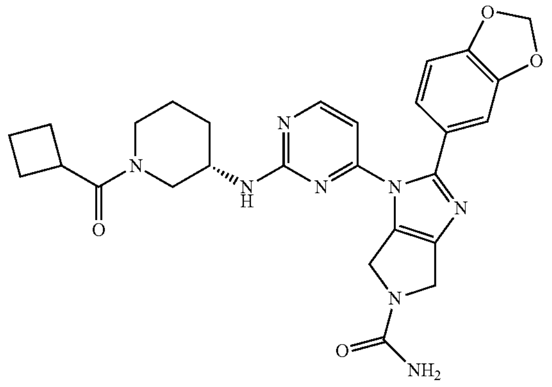
16m
Compound 16m (29%) was obtained by performing synthesis and purification in the same manner as in Example 2.
1H NMR (400 MHz, MeOD) δ 8.28-8.14 (m, 1H), 7.03-6.83 (m, 3H), 6.20 (d, J=61.5 Hz, 3H), 4.80 (s, 2H), 4.48 (s, 2H), 4.06 (d, J=81.6 Hz, 2H), 3.13-3.02 (m, 1H), 2.94 (s, 1H), 2.15-1.43 (m, 12H).

<Example 14> (S)-1-(2-((1-(cyclopropanecarbonyl)piperidin-3-yl)amino)pyrimidin-4-yl)-2-(2,3-dihydrobenzofuran-5-yl)-4,6-dihydropyrrolo[3,4-d]imidazole-5(1H)-carboxamide (Compound 16n)
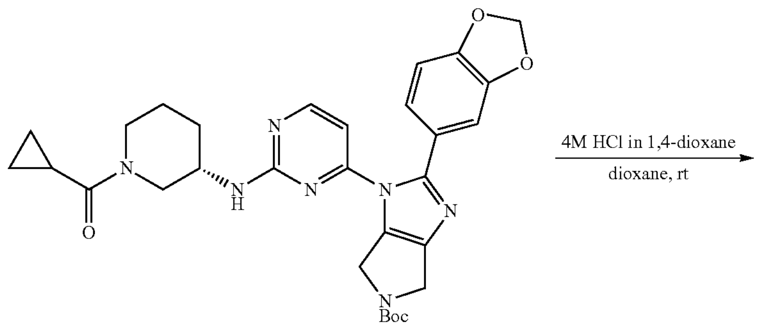
14n
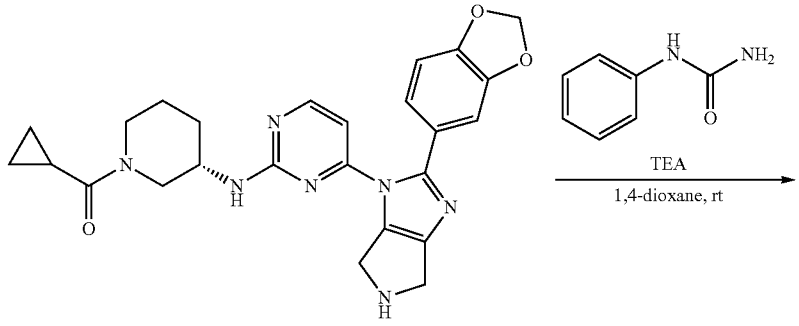
15n
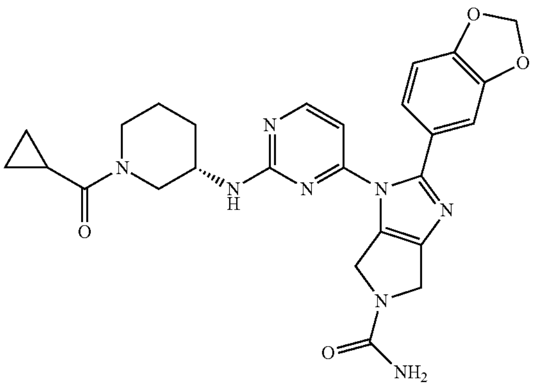
16n
Compound 16n (40%) was obtained by performing synthesis and purification in the same manner as in Example 2.
1H NMR (400 MHz, MeOD) δ 8.24-8.09 (m, 1H), 7.32 (s, 1H), 7.19 (d, J=7.8 Hz, 1H), 6.78 (d, J=8.1 Hz, 1H), 6.17 (d, J=77.2 Hz, 1H), 4.77 (s, 2H), 4.61 (t, J=8.8 Hz, 2H), 4.48 (d, J=2.8 Hz, 2H), 4.26-3.52 (m, 3H), 3.23 (dd, J=10.2, 8.0 Hz, 2H), 2.19-1.43 (m, 6H), 1.31 (dd, J=12.7, 5.3 Hz, 1H), 0.81 (ddd, J=94.9, 52.5, 36.9 Hz, 4H).

<Example 15> (R)-1-(2-((1-(cyclopropanecarbonyl) pyrrolidin-3-yl)amino)pyrimidin-4-yl)-2-(2,3-dihydrobenzofuran-5-yl)-4,6-dihydropyrrolo[3,4-d]imidazole-5(1H)-carboxamide (Compound 160)
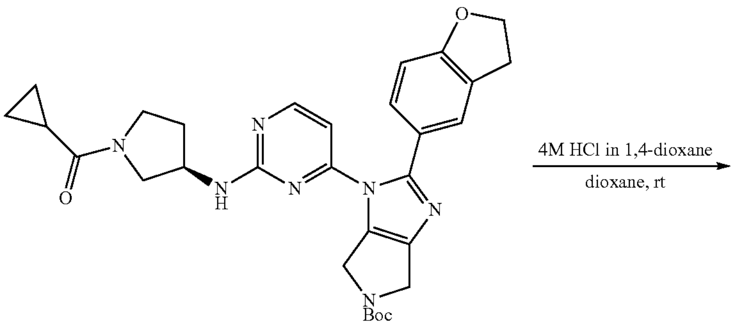
14o
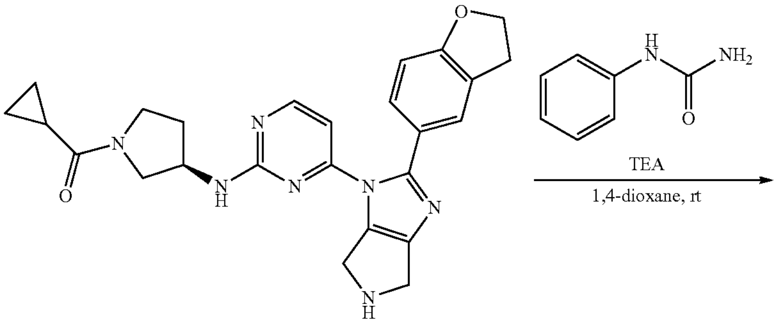
15o
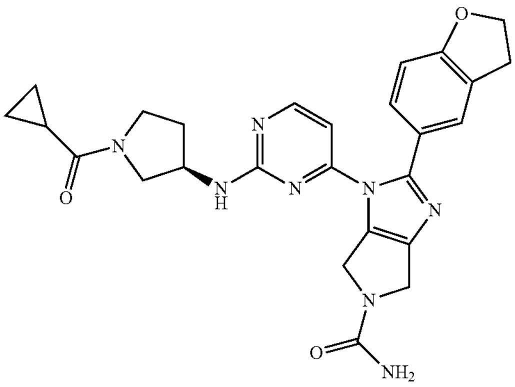
16o
Compound 16o (40%) was obtained by performing synthesis and purification in the same manner as in Example 2.
1H NMR (400 MHz, MeOD) δ 8.17 (dd, J=12.3, 5.4 Hz, 1H), 7.33 (dd, J=5.0, 1.3 Hz, 1H), 7.19 (d, J=8.3 Hz, 1H), 6.79 (dd, J=8.3, 1.6 Hz, 1H), 6.13 (s, 1H), 4.77 (s, 2H), 4.61 (td, J=8.8, 2.0 Hz, 2H), 4.48 (d, J=2.8 Hz, 2H), 4.37 (s, 1H), 3.83 (dddd, J=29.1, 23.2, 18.4, 16.3 Hz, 2H), 3.68-3.38 (m, 2H), 3.23 (t, J=8.7 Hz, 2H), 2.36-1.95 (m, 2H), 1.87-1.71 (m, 1H), 0.97-0.76 (m, 4H).

<Example 16> (S)-1-(2-((1-(cyclopropanecarbonyl) pyrrolidin-3-yl)amino)pyrimidin-4-yl)-2-(2,3-dihydrobenzofuran-5-yl)-4,6-dihydropyrrolo[3,4-d]imidazole-5(1H)-carboxamide (16p)

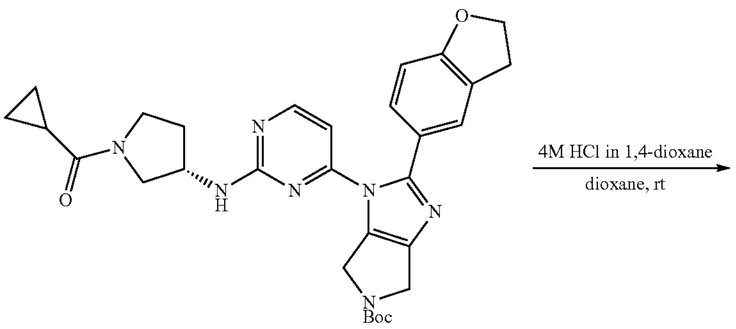

14p

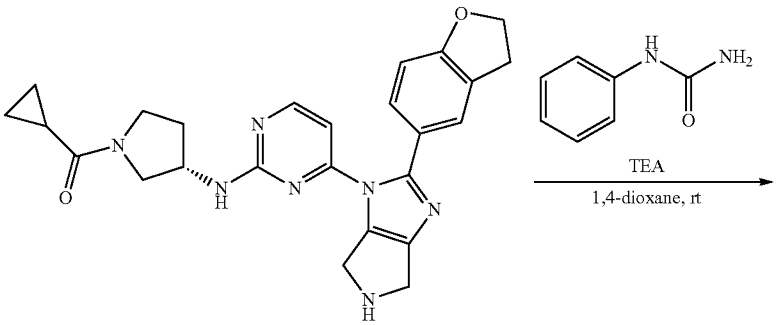

15p

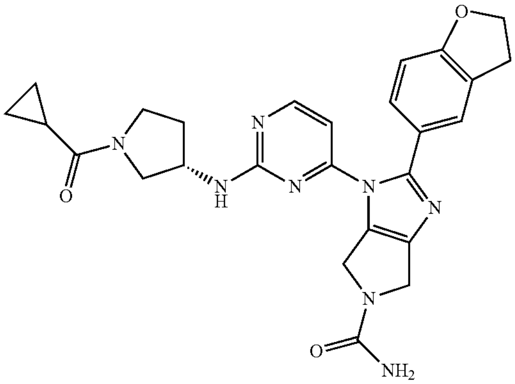

16p

Compound 16p (30%) was obtained by performing synthesis and purification in the same manner as in Example 2.

1H NMR (400 MHz, MeOD) δ 8.18 (dd, J=12.2, 5.4 Hz, 1H), 7.34 (d, J=3.8 Hz, 1H), 7.20 (d, J=8.3 Hz, 1H), 6.79 (dd, J=8.3, 1.6 Hz, 1H), 6.13 (s, 1H), 4.78 (s, 2H), 4.61 (td, J=8.8, 2.0 Hz, 2H), 4.48 (s, 2H), 4.38 (s, 1H), 4.07-3.69 (m, 2H), 3.65-3.38 (m, 2H), 3.23 (t, J=8.7 Hz, 2H), 2.36-1.95 (m, 2H), 1.79 (dddd, J=29.6, 12.7, 7.9, 4.7 Hz, 1H), 0.96-0.77 (m, 4H).

The synthesis methods of the Preparation Examples and Examples can be expressed as the following Reaction Scheme 1.

[Reaction Scheme 1]
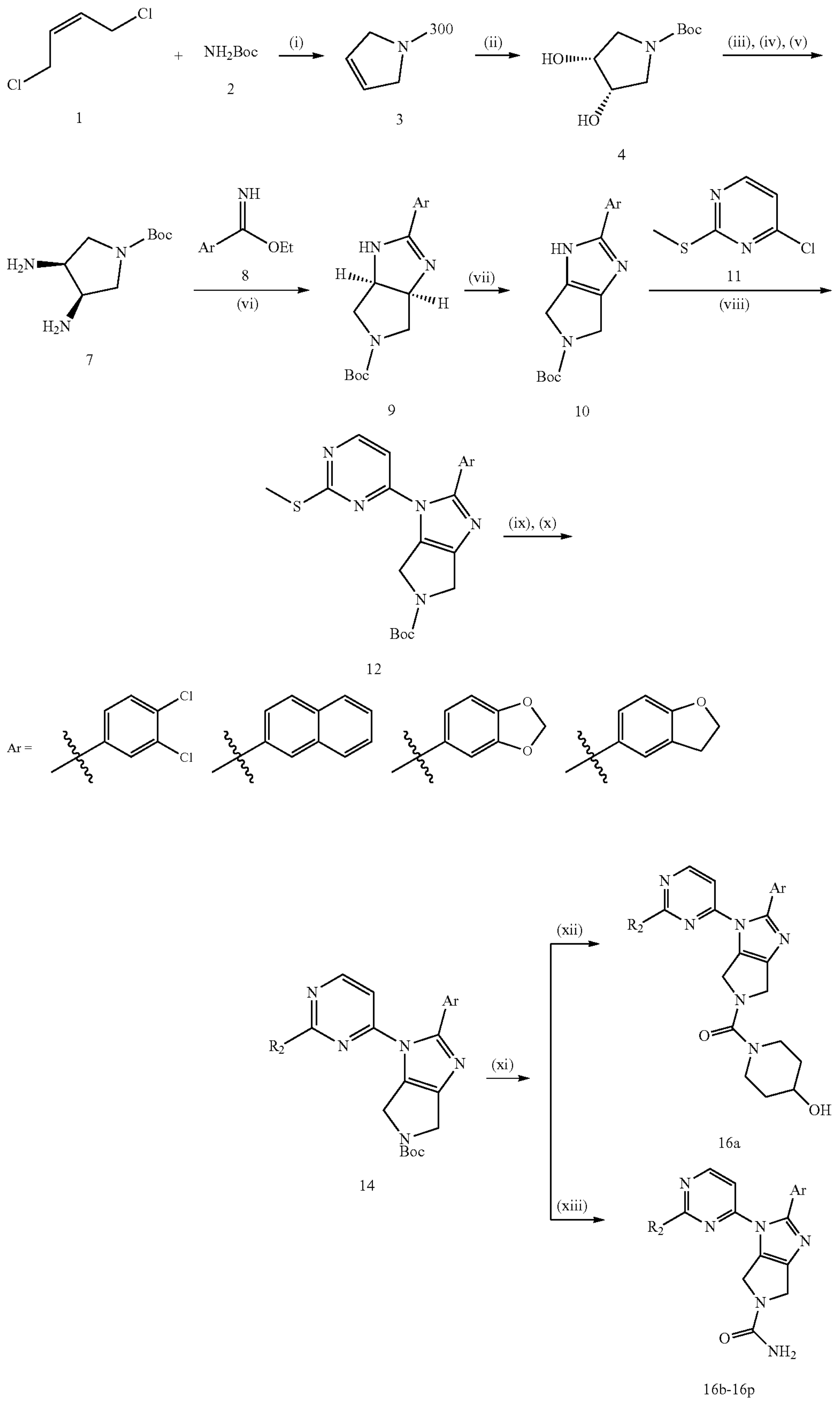

-continued
$R_2$ = 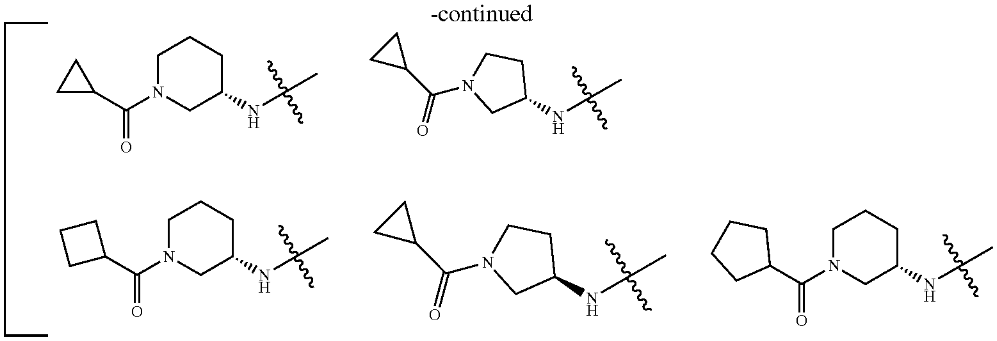
Experimental Example 1. Measurement of JNK3 Enzyme Activity
A change in JNK3 enzyme activity by treatment with the imidazole derivatives of the following Tables 1 and 2 according to the present invention was confirmed by $IC_{50}$.
TABLE 1
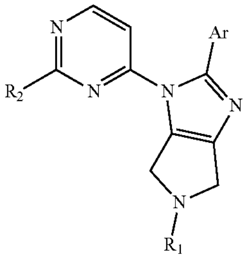
| Compound No. | Ar | $R_1$ | $R_2$ | $IC_{50}$ (nM) |
|---|---|---|---|---|
| 16a | 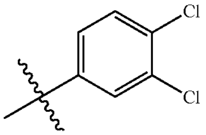 [SMILES: *c1ccc(Cl)c(Cl)c1] | 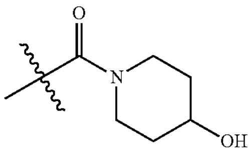 [SMILES: *C(=O)N1CCC(O)CC1] | 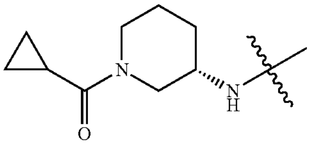 [SMILES: *N[C@H]1CCCN(C(=O)C2CC2)C1] | +++ |
| 16b | | 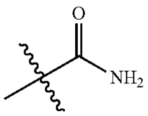 [SMILES: *C(N)=O] | 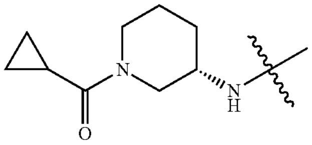 [SMILES: *N[C@H]1CCCN(C(=O)C2CC2)C1] | +++ |
| 16c | | | 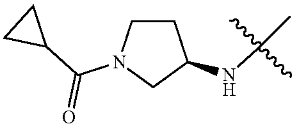 [SMILES: *N[C@@H]1CCN(C(=O)C2CC2)C1] | +++ |
| 16d | | | 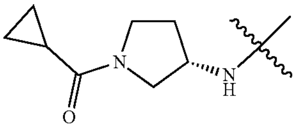 [SMILES: *N[C@H]1CCN(C(=O)C2CC2)C1] | ++ |
| 16e | | | 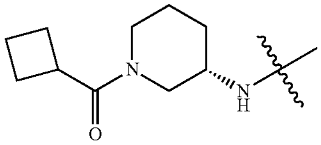 [SMILES: *N[C@H]1CCCN(C(=O)C2CCC2)C1] | +++ |

TABLE 1-continued
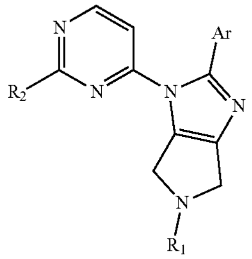
| Compound No. | Ar | $R_1$ | $R_2$ | $IC_{50}$ (nM) |
|---|---|---|---|---|
| 16f | | | 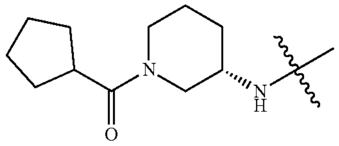 [SMILES: *N[C@H]1CCCN(C(=O)C2CCCC2)C1] | +++ |
| 16g | 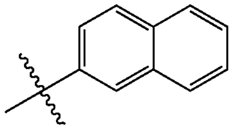 [SMILES: *c1ccc2ccccc2c1] | | 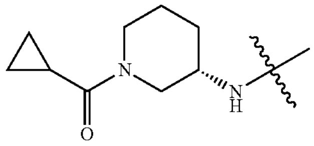 [SMILES: *N[C@H]1CCCN(C(=O)C2CC2)C1] | +++ |
| 16h | | | 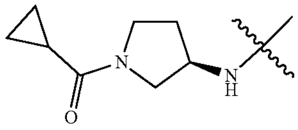 [SMILES: *N[C@@H]1CCN(C(=O)C2CC2)C1] | +++ |
| 16l | | | 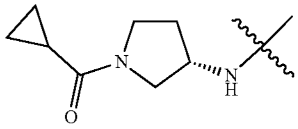 [SMILES: *N[C@H]1CCN(C(=O)C2CC2)C1] | +++ |
Activity
−: >10 uM/
+: 1 uM/
++: 0.1~0.03 uM/
+++: <30 nM
TABLE 2
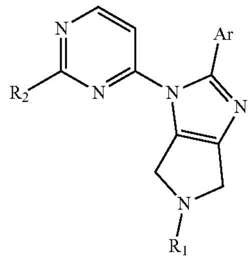
| Compound No. | Ar | $R_1$ | $R_2$ | $IC_{50}$ (nM) |
|---|---|---|---|---|
| 16j | 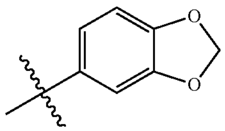 [SMILES: *c1ccc2c(c1)OCO2] | 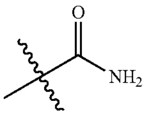 | 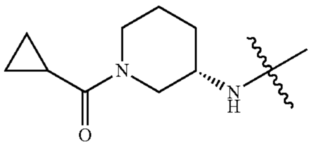 [SMILES: *N[C@H]1CCCN(C(=O)C2CC2)C1] | ++ |

TABLE 2-continued

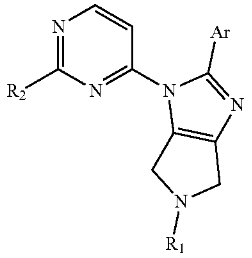

| Compound No. | Ar | $R_1$ | $R_2$ | $IC_{50}$ (nM) |
|---|---|---|---|---|
| 16k | | | 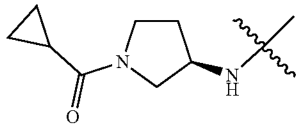 [SMILES: *N[C@@H]1CCN(C(=O)C2CC2)C1] | ++ |
| 16l | | | 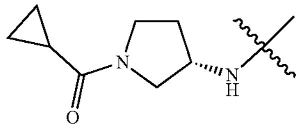 [SMILES: *N[C@H]1CCN(C(=O)C2CC2)C1] | + |
| 16m | | | 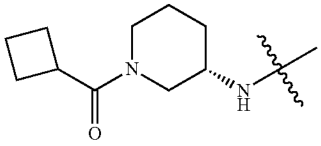 [SMILES: *N[C@H]1CCCN(C(=O)C2CCC2)C1] | + |
| 16n | 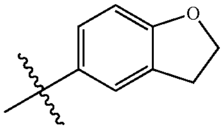 [SMILES: *c1ccc2c(c1)CCO2] | | 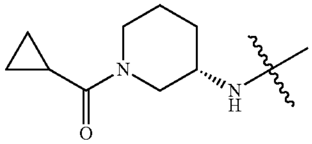 [SMILES: *N[C@H]1CCCN(C(=O)C2CC2)C1] | ++ |
| 16o | | | 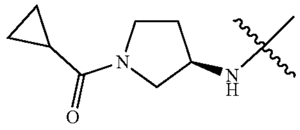 [SMILES: *N[C@@H]1CCN(C(=O)C2CC2)C1] | +++ |
| 16p | | | 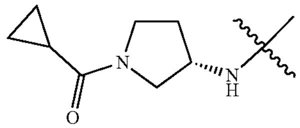 [SMILES: *N[C@H]1CCN(C(=O)C2CC2)C1] | + |
| | | Control substance JNK1 VN | | 5 |

Activity
–: >10 uM/
+: 1 uM/
++: 0.1~0.03 uM/
+++: <30 nM

The $IC_{50}$ values of JNK3 of the synthesized compounds were measured, and are summarized as shown in Tables 1 and 2.

Kinase panel screening of Compound 16c for 38 different kinases at a single dose concentration of 10 μM was performed, and is shown in FIG. 1. As a result of the analysis, Compound 16c did not show a selective profile result of JNK3, but showed 100% inhibitory activity for JNK2 and JNK3, 70% inhibitory activity for GSK-β and 50% inhibitory activity for RIPK3 in the case of JNK2, JNK3, GSK-β and RIPK3.

The above-described description of the present invention is provided for illustrative purposes, and those skilled in the art to which the present invention pertains will understand that the present invention can be easily modified into other specific forms without changing the technical spirit or essential features of the present invention. Therefore, it should be understood that the above-described embodiments are only exemplary in all aspects and are not restrictive.

The invention claimed is:

1. A compound of the following Chemical Formula 1 or a pharmaceutically acceptable salt thereof:

[Chemical Formula 1]

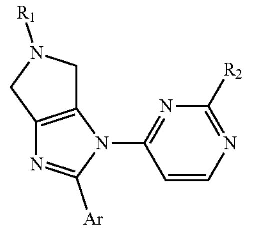

in Chemical Formula 1, $R_1$ is selected from the group consisting of

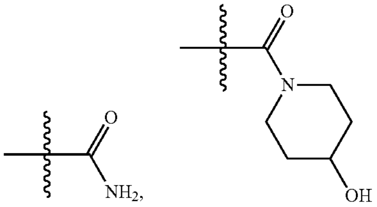

and a $C_1$-$C_6$ alkyl, $R_2$ is

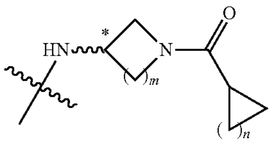

herein, n is an integer from 1 to 4, m is an integer from 2 to 3, carbon denoted as * is a chiral carbon, Ar is selected from the group consisting of

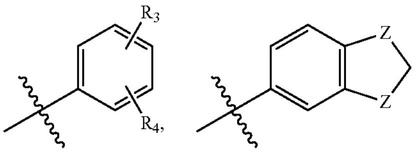

and naphthalenyl, $R_3$ and $R_4$ are each independently a halogen atom, and

Z is a carbon or oxygen atom.

2. The compound of claim 1, wherein the compound of Chemical Formula 1 has a structure of the following Chemical Formula 2:

[Chemical Formula 2]

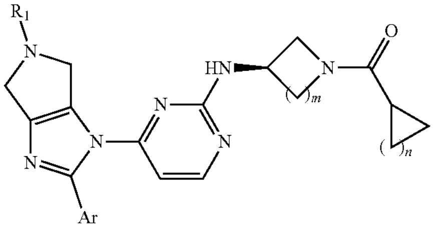

in Chemical Formula 2, $R_1$ is selected from the group consisting of

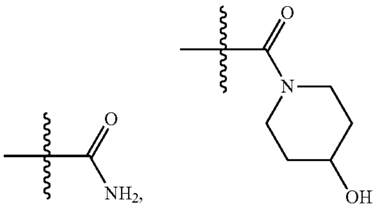

and a $C_1$-$C_6$ alkyl, n is an integer from 1 to 4, m is an integer from 2 to 3, Ar is selected from the group consisting of

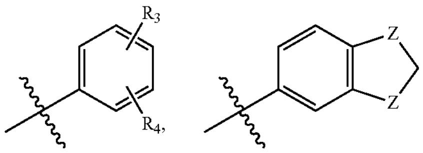

and naphthalenyl, $R_3$ and $R_4$ are each independently a halogen atom, and

Z is a carbon or oxygen atom.

3. The compound of claim 1, wherein the compound of Chemical Formula 1 has a structure of the following Chemical Formula 3:

[Chemical Formula 3]

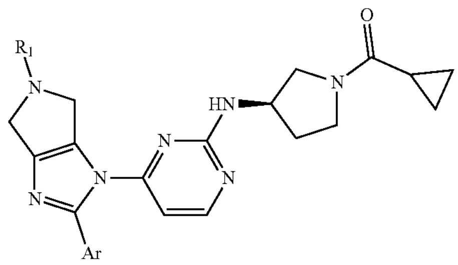

in Chemical Formula 3, $R_1$ is selected from the group consisting of

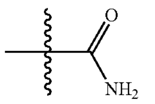

and a $C_1$-$C_6$ alkyl,

Ar is selected from the group consisting of

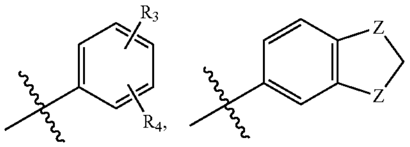

and naphthalenyl, $R_3$ and $R_4$ are each independently a halogen atom, and

Z is a carbon or oxygen atom.

4. The compound of claim 1, wherein the compound of Chemical Formula 1 has a structure of the following Chemical Formula 4:

[Chemical Formula 4]

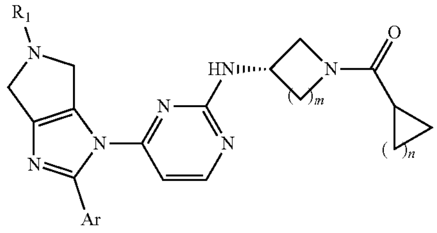

in Chemical Formula 4, $R_1$ is selected from the group consisting of

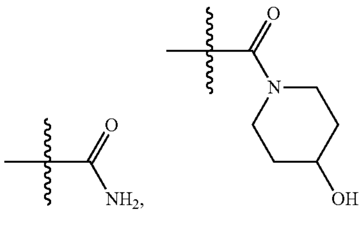

and a $C_1$-$C_6$ alkyl, n is an integer from 1 to 4, m is an integer from 2 to 3, Ar is selected from the group consisting of

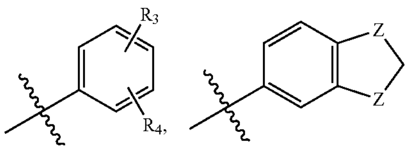

and naphthalenyl, $R_3$ and $R_4$ are each independently a halogen atom, and

Z is a carbon or oxygen atom.

5. The compound of claim 1, wherein the compound of Chemical Formula 1 has a structure of the following Chemical Formula 5:

[Chemical Formula 5]

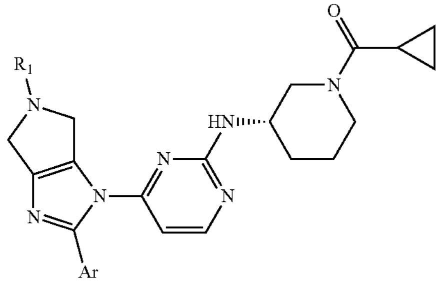

in Chemical Formula 5, $R_1$ is selected from the group consisting of

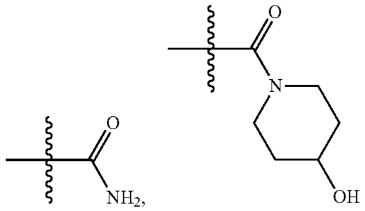

and a $C_1$-$C_6$ alkyl,

Ar is selected from the group consisting of

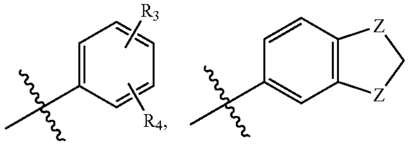

and naphthalenyl, $R_3$ and $R_4$ are each independently a halogen atom, and

Z is a carbon or oxygen atom.

6. The compound of claim 1, wherein the compound of Chemical Formula 1 has a structure of the following Chemical Formula 6:

[Chemical Formula 6]

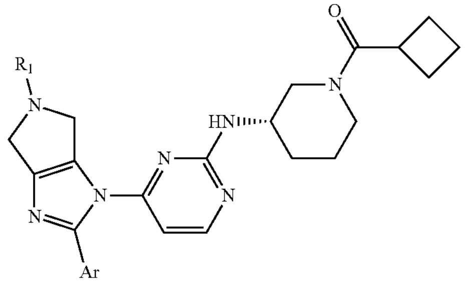

in Chemical Formula 6, $R_1$ is selected from the group consisting of

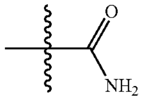

and a $C_1$-$C_6$ alkyl,

Ar is selected from the group consisting of

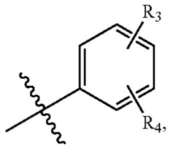

and

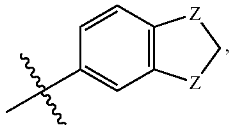

$R_3$ and $R_4$ are each independently a halogen atom, and

Z is a carbon or oxygen atom.

7. The compound of claim 1, wherein the compound of Chemical Formula 1 has a structure of the following Chemical Formula 7:

[Chemical Formula 7]

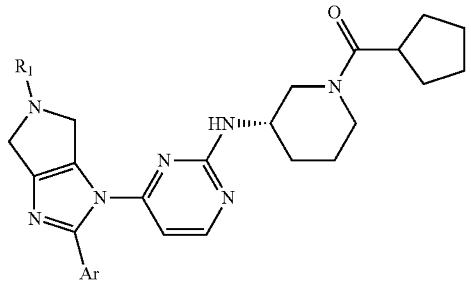

in Chemical Formula 7, $R_1$ is selected from the group consisting of

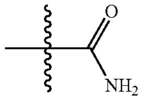

and a $C_1$-$C_6$ alkyl,

Ar is

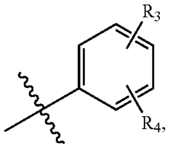

and $R_3$ and $R_4$ are each independently a halogen atom.

8. The compound of claim 1, wherein the compound of Chemical Formula 1 has a structure of the following Chemical Formula 8:

[Chemical Formula 8]

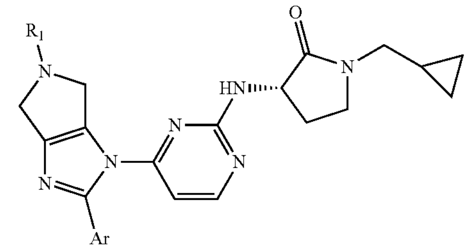

in Chemical Formula 8, $R_1$ is selected from the group consisting of

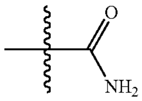

and a $C_1$-$C_6$ alkyl,

Ar is selected from the group consisting of

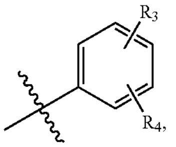

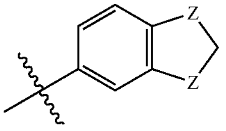

and naphthalenyl, $R_3$ and $R_4$ are each independently a halogen atom, and

Z is a carbon or oxygen atom.

9. The compound of claim 1, wherein the compound of Chemical Formula 1 is (S)-(1-(2-((1-(cyclopropanecarbonyl)piperidin-3-yl)amino)pyrimidin-4-yl)-2-(3,4-dichlorophenyl)-4,6-dihydropyrrolo[3,4-d]imidazol-5(1H)-yl)(4-hydroxypiperidin-1-yl)methanone;

(S)-(1-(2-((1-(cyclopropanecarbonyl)piperidin-3-yl)amino)pyrimidin-4-yl)-2-(3,4-dichlorophenyl)-4,6-dihydropyrrolo[3,4-d]imidazol-5(1H)-carboxamide;

(R)-1-(2-((1-(cyclopropanecarbonyl)pyrrolidin-3-yl)amino)pyrimidin-4-yl)-2-(3,4-dichlorophenyl)-4,6-dihydropyrrolo[3,4-d]imidazol-5(1H)-carboxamide;

(S)-1-(2-((1-(cyclopropanecarbonyl)pyrrolidin-3-yl)amino)pyrimidin-4-yl)-2-(3,4-dichlorophenyl)-4,6-dihydropyrrolo[3,4-d]imidazole-5(1H)-carboxamide;

(S)-1-(2-((1-(cyclobutanecarbonyl)piperidin-3-yl)amino)pyrimidin-4-yl)-2-(3,4-dichlorophenyl)-4,6-dihydropyrrolo[3,4-d]imidazole-5(1H)-carboxamide;

(S)-1-(2-((1-(cyclopentanecarbonyl)piperidin-3-yl)amino)pyrimidin-4-yl)-2-(3,4-dichlorophenyl)-4,6-dihydropyrrolo[3,4-d]imidazole-5(1H)-carboxamide;

(S)-1-(2-((1-(cyclopropanecarbonyl)piperidin-3-yl)amino)pyrimidin-4-yl)-2-(naphthalen-2-yl)-4,6-dihydropyrrolo[3,4-d]imidazole-5(1H)-carboxamide;

(R)-1-(2-((1-(cyclopropanecarbonyl)pyrrolidin-3-yl)amino)pyrimidin-4-yl)-2-(naphthalen-2-yl)-4,6-dihydropyrrolo[3,4-d]imidazole-5(1H)-carboxamide;

(S)-1-(2-((1-(cyclopropanecarbonyl)pyrrolidin-3-yl)amino)pyrimidin-4-yl)-2-(3,4-dichlorophenyl)-4,6-dihydropyrrolo[3,4-d]imidazole-5(1H)-carboxamide;

(S)-2-(benzo[d][1,3]dioxol-5-yl)-1-(2-((1-(cyclopropanecarbonyl)piperidin-3-yl)amino)pyrimidin-4-yl)-4,6-dihydropyrrolo[3,4-d]imidazole-5(1H)-carboxamide;

(R)-2-(benzo[d][1,3]dioxol-5-yl)-1-(2-((1-(cyclopropanecarbonyl)pyrrolidin-3-yl)amino)pyrimidin-4-yl)-4,6-dihydropyrrolo[3,4-d]imidazole-5(1H)-carboxamide;

(S)-2-(benzo[d][1,3]dioxol-5-yl)-1-(2-((1-(cyclopropanecarbonyl)pyrrolidin-3-yl)amino)pyrimidin-4-yl)-4,6-dihydropyrrolo[3,4-d]imidazole-5(1H)-carboxamide;

(S)-2-(benzo[d][1,3]dioxol-5-yl)-1-(2-((1-(cyclobutanecarbonyl)piperidin-3-yl)amino)pyrimidin-4-yl)-4,6-dihydropyrrolo[3,4-d]imidazole-5(1H)-carboxamide;

(S)-1-(2-((1-(cyclopropanecarbonyl)piperidin-3-yl)amino)pyrimidin-4-yl)-2-(2,3-dihydrobenzofuran-5-yl)-4,6-dihydropyrrolo[3,4-d]imidazole-5(1H)-carboxamide;

(R)-1-(2-((1-(cyclopropanecarbonyl)pyrrolidin-3-yl)amino)pyrimidin-4-yl)-2-(2,3-dihydrobenzofuran-5-yl)-4,6-dihydropyrrolo[3,4-d]imidazole-5(1H)-carboxamide; or (S)-1-(2-((1-(cyclopropanecarbonyl)pyrrolidin-3-yl)amino)pyrimidin-4-yl)-2-(2,3-dihydrobenzofuran-5-yl)-4,6-dihydropyrrolo[3,4-d]imidazole-5(1H)-carboxamide.

10. A pharmaceutical composition for preventing or treating a degenerative brain disease, comprising the compound or the pharmaceutically acceptable salt thereof according to claim 1 as an active ingredient.

11. A method for treating a degenerative brain disease, comprising administering an effective amount of the compound or the pharmaceutically acceptable salt thereof according to claim 1 to a subject in need thereof.

12. The method of claim 11, wherein the degenerative brain disease is Alzheimer's dementia or Parkinson's disease.

13. The method of claim 11, wherein the compound inhibits the activity of c-Jun N-terminal kinase 3 (JNK3).

* * * * *